United States Patent [19]

Matsuo et al.

[11] Patent Number: 5,661,159
[45] Date of Patent: Aug. 26, 1997

[54] QUINOLYLBENZOFURAN DERIVATIVES AS LEUKOTRIENE ANTAGONISTS

[75] Inventors: Masaaki Matsuo, Toyonaka; Kazuo Okumura, Osaka; Shinji Shigenaga, Kobe, all of Japan

[73] Assignee: Fujisawa Pharmaceutical Co., Ltd., Osaka, Japan

[21] Appl. No.: 256,735

[22] PCT Filed: Feb. 18, 1993

[86] PCT No.: PCT/JP93/00198

§ 371 Date: Aug. 2, 1994

§ 102(e) Date: Aug. 2, 1994

[87] PCT Pub. No.: WO93/17013

PCT Pub. Date: Sep. 2, 1993

[30] Foreign Application Priority Data

Feb. 21, 1992 [GB] United Kingdom ............ 9203798

[51] Int. Cl.$^6$ .................. A61K 31/47; C07D 401/04
[52] U.S. Cl. ........................... 514/314; 546/167
[58] Field of Search ............ 548/253; 514/382, 514/314; 546/167

[56] References Cited

PUBLICATIONS

Chemical Abstracts, vol. 72, 1970, abstract 31573e.
Musser, J.H. Journal of Medicinal Chemistry, vol. 33, No. 1 1990, pp. 240–245.
Shaw, A. Journal of Medicinal Chemistry, vol. 34, NO. 4 1991, pp. 1235–1242.

*Primary Examiner*—Jacqueline Haley
*Attorney, Agent, or Firm*—Oblon, Spivak, McClelland, Maier & Neustadt, P.C.

[57] ABSTRACT

This invention relates to new quinolylbenzofuran derivatives having activities as leukotrien and Slow Reacting Substance of Anaphylaxis antagonists and inhibitors and represented by the general formula (I):

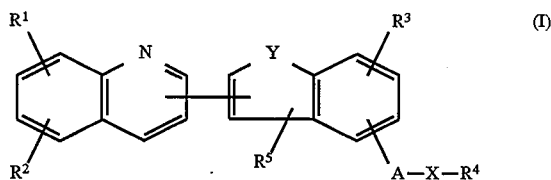

wherein $R^1$ is halogen, etc., $R^2$ is hydrogen or halogen, $R^3$ is hydrogen, halogen, hydroxy, lower alkyl or lower alkoxy, $R^4$ is hydrogen, acyl, cyano, nitro, substituted or unsubstituted aryl, or substituted or unsubstituted lower alkyl, $R^5$ is hydrogen, hydroxy, lower alkyl or lower alkoxy, A is lower alkylene, lower alkenylene or a single bond, X is a single bond, O, NH, S, SO or $SO_2$, and Y is O or S, provided that when $R^3$ is hydrogen, $R^4$ is hydrogen, $R^5$ is hydrogen, A is a single bond and X is a single bond, then $R^1$ is halogen, etc., and pharmaceutically acceptable salts thereof to processes for the preparation thereof and to a pharmaceutical composition comprising the same.

5 Claims, No Drawings

QUINOLYLBENZOFURAN DERIVATIVES AS LEUKOTRIENE ANTAGONISTS

This is a National State application of PCT/JP93/00198 filed Feb. 18, 1993, published as WO93/17013 on Sep. 2, 1993.

TECHNICAL FIELD

This invention relates to new quinolylbenzofuran derivatives and pharmaceutically acceptable salts thereof which are useful as a medicament.

BACKGROUND ART

Some quinolylbenzofuran derivatives have been known as described, for example, in J. Chem. Soc., 1964, 173 and Chim. Ther., 6, 159 (1971).

DISCLOSURE OF INVENTION

This invention relates to new quinolylbenzofuran derivatives and pharmaceutically acceptable salts thereof.

More particularly, it relates to new quinolylbenzofuran derivatives and pharmaceutically acceptable salts thereof which have activities as leukotriene and Slow Reacting Substance of Anaphylaxis (hereinafter, SRS-A) antagonists or inhibitors, to processes for preparation thereof, to a pharmaceutical composition comprising the same, and to methods of using the same therapeutically in the prevention and/or treatment of allergy or inflammation in human beings or animals, and more particularly to methods for prevention and/or treatment of asthma, psoriasis, hepatitis, pancreatitis, arthritis, nephritis, inflammatory bowel disease, septic Shock, arteriosclerosis, myocardial infarction, cerebral vasospasm, rhinitis, conjunctivitis, dermatitis, rheumatism, peptic ulcer, gout and the like.

One object of this invention is to provide new and useful quinolylbenzofuran derivatives and pharmaceutically acceptable salts thereof which possess activities as leukotriene and SRS-A antagonists or inhibitors.

Another object of this invention is to provide processes for the preparation of said derivatives and salts thereof.

A further object of this invention is to provide a pharmaceutical composition comprising, as an active ingredient, said quinolylbenzofuran derivatives and pharmaceutically acceptable salt thereof.

Still further object of this invention is to provide a therapeutical method for the prevention and/or treatment of allergy or inflammation, and more particularly of asthma, psoriasis, hepatitis, pancreatitis, arthritis, nephritis, inflammatory bowel disease, septic shock, arteriosclerosis, myocardial infarction, cerebral vasospasm, rhinitis, conjunctivitis, dermatitis, rheumatism, peptic ulcer, gout and the like, using said quinolylbenzofuran derivatives and pharmaceutically acceptable salts thereof.

The object quinolylbenzofuran derivatives of this invention are new and can be represented by the following general formula (I) :

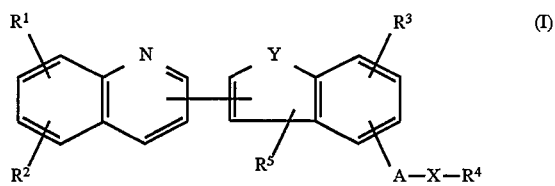

wherein $R^1$ is hydrogen; halogen; lower alkyl optionally substituted with halogen, lower alkylamino or lower alkyl (acyl)amino; cyclo(lower)alkyl; tricycloalkyl; aryl optionally substituted with lower alkoxy; or a heterocyclic group;

$R^2$ is hydrogen or halogen, $R^3$ is hydrogen, halogen, hydroxy, lower alkyl or lower alkoxy, $R^4$ is hydrogen; acyl; cyano; nitro; aryl optionally substituted with hydroxy(lower)-alkyl, halo(lower)alkyl, cyano(lower)alkyl, heterocyclic(lower) alkyl or acyl; or lower alkyl which may be substituted with substituent(s) selected from the group consisting of halogen, cyano, hydroxy, lower alkylsulfonyloxy, arylsulfonyloxy, acyl, lower alkylthio, acyl(lower) alkylthio, heterocyclic(lower)alkylthio and aryl optionally substituted with halo(lower)alkyl, cyano(lower) alkyl, heterocyclic(lower)alkyl, cyano, acyl, acyl (lower)alkyl or a heterocyclic group;

$R^5$ is hydrogen, hydroxy, lower alkyl or lower alkoxy,

A is lower alkylene, lower alkenylene or a single bond,

X is a single bond, O, NH, S, SO or $SO_2$, and

Y is O or S, provided that when $R^3$ is hydrogen, $R^4$ is hydrogen, $R^5$ is hydrogen, A is a single bond and X is a single bond, then $R^1$ is halogen; lower alkyl substituted with halogen, lower alkylamino or lower alkyl(acyl)amino; cyclo(lower)alkyl; tricycloalkyl; aryl substituted with lower alkoxy; or a heterocyclic group;

and pharmaceutically acceptable salts thereof.

The object compound (I) or its salt can be prepared by processes as illustrated in the following reaction schemes.

Process 1

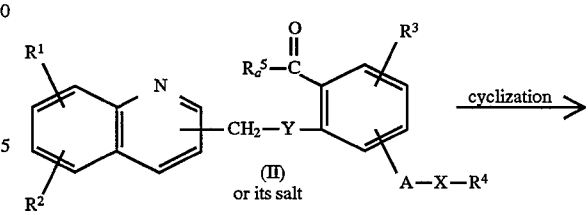

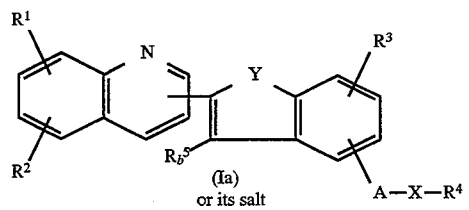

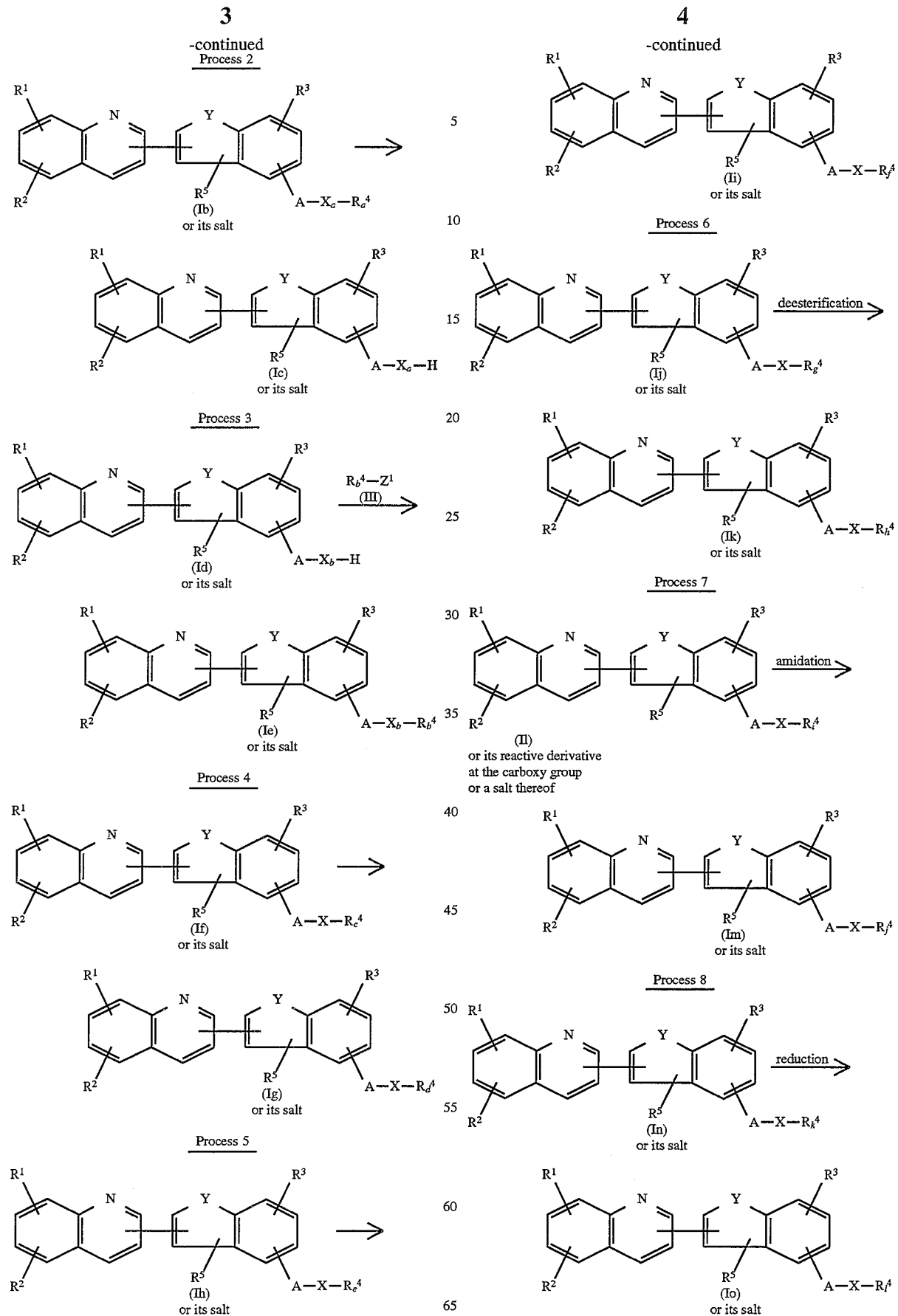

-continued
Process 9
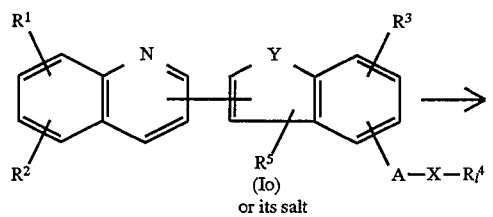
(Io) or its salt
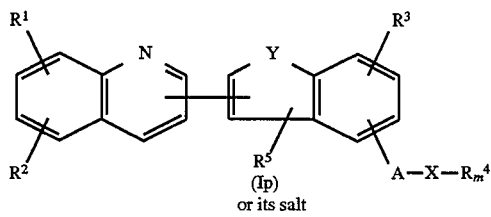
(Ip) or its salt
Process 10
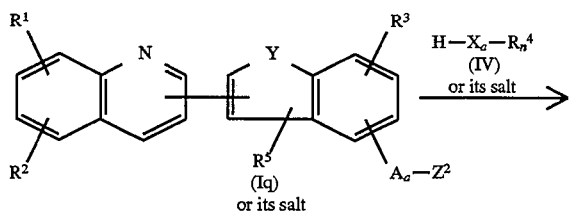
(Iq) or its salt
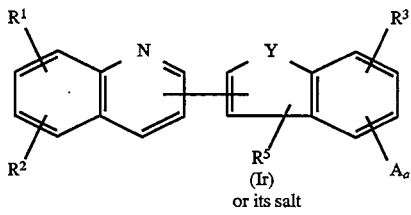
(Ir) or its salt
Process 11
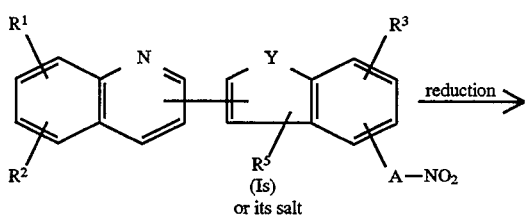
(Is) or its salt
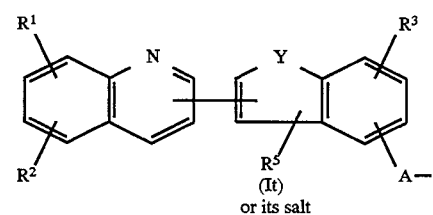
(It) or its salt
Process 12
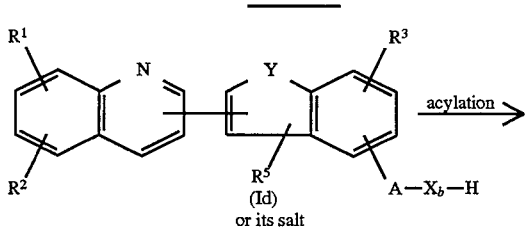
(Id) or its salt
-continued
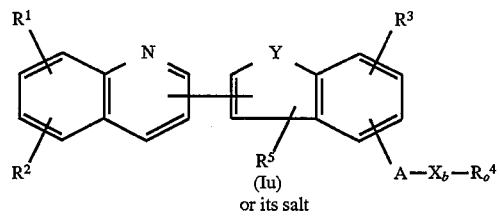
(Iu) or its salt
Process 13
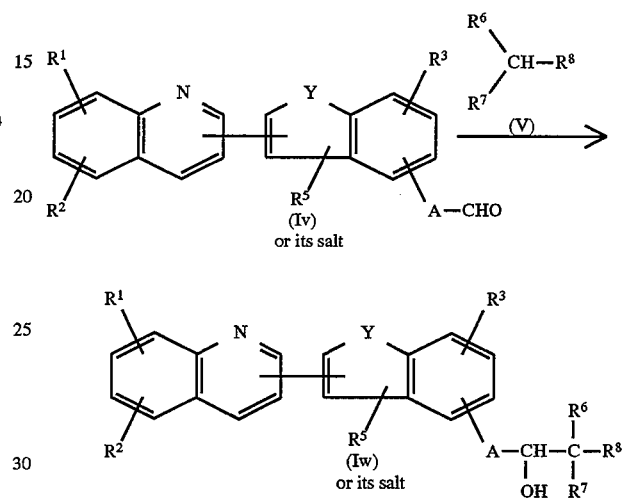
(Iv) or its salt
(Iw) or its salt
Process 14
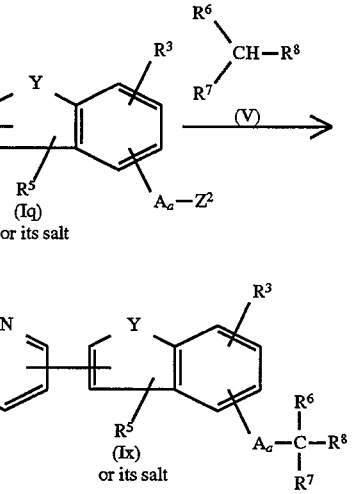
(Iq) or its salt
(Ix) or its salt
Process 15
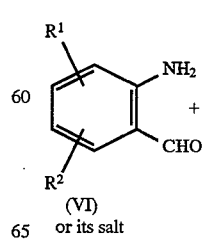
(VI) or its salt

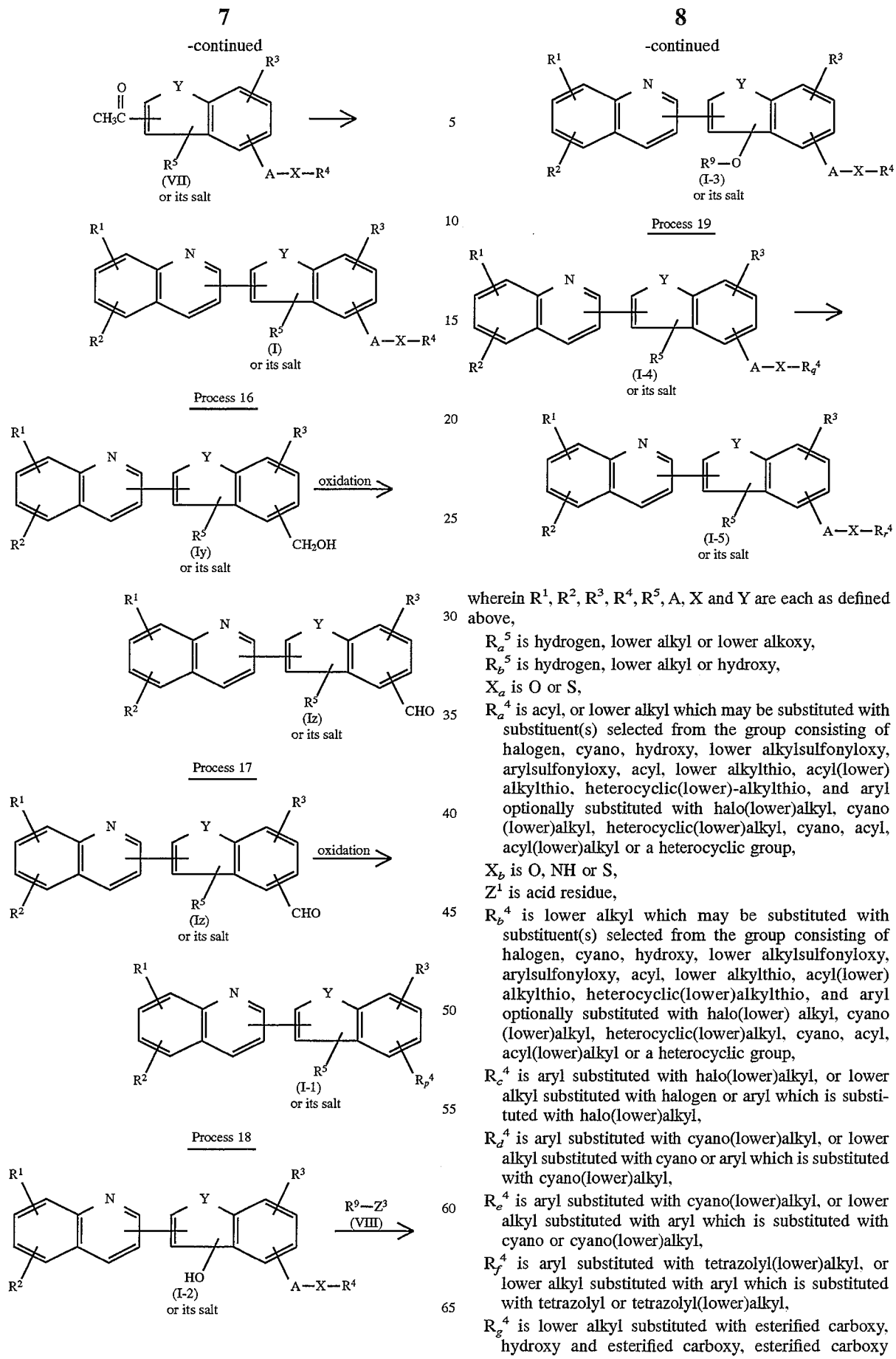

wherein $R^1$, $R^2$, $R^3$, $R^4$, $R^5$, A, X and Y are each as defined above, $R_a^5$ is hydrogen, lower alkyl or lower alkoxy, $R_b^5$ is hydrogen, lower alkyl or hydroxy, $X_a$ is O or S, $R_a^4$ is acyl, or lower alkyl which may be substituted with substituent(s) selected from the group consisting of halogen, cyano, hydroxy, lower alkylsulfonyloxy, arylsulfonyloxy, acyl, lower alkylthio, acyl(lower)alkylthio, heterocyclic(lower)-alkylthio, and aryl optionally substituted with halo(lower)alkyl, cyano (lower)alkyl, heterocyclic(lower)alkyl, cyano, acyl, acyl(lower)alkyl or a heterocyclic group, $X_b$ is O, NH or S, $Z^1$ is acid residue, $R_b^4$ is lower alkyl which may be substituted with substituent(s) selected from the group consisting of halogen, cyano, hydroxy, lower alkylsulfonyloxy, arylsulfonyloxy, acyl, lower alkylthio, acyl(lower)alkylthio, heterocyclic(lower)alkylthio, and aryl optionally substituted with halo(lower) alkyl, cyano (lower)alkyl, heterocyclic(lower)alkyl, cyano, acyl, acyl(lower)alkyl or a heterocyclic group, $R_c^4$ is aryl substituted with halo(lower)alkyl, or lower alkyl substituted with halogen or aryl which is substituted with halo(lower)alkyl, $R_d^4$ is aryl substituted with cyano(lower)alkyl, or lower alkyl substituted with cyano or aryl which is substituted with cyano(lower)alkyl, $R_e^4$ is aryl substituted with cyano(lower)alkyl, or lower alkyl substituted with aryl which is substituted with cyano or cyano(lower)alkyl, $R_f^4$ is aryl substituted with tetrazolyl(lower)alkyl, or lower alkyl substituted with aryl which is substituted with tetrazolyl or tetrazolyl(lower)alkyl, $R_g^4$ is lower alkyl substituted with esterified carboxy, hydroxy and esterified carboxy, esterified carboxy (lower)alkylthio, esterified carboxy(lower)alkylthio and lower alkylcarbamoyl(lower)alkylthio, lower alkylthio and esterified carboxy(lower)alkylthio or aryl which is substituted with esterified carboxy or esterified carboxy(lower)alkyl, $R_h^4$ is lower alkyl substituted with carboxy hydroxy and carboxy, carboxy(lower)alkylthio, carboxy(lower) alkylthio and lower alkylcarbamoyl(lower)alkylthio, lower alkylthio and carboxy(lower)alkylthio or aryl which is substituted with carboxy or carboxy(lower) alkyl, $R_i^4$ is lower alkyl substituted with carboxy or aryl substituted with carboxy or carboxy(lower)alkyl, $R_j^4$ is lower alkyl substituted with carbamoyl which may be substituted with lower alkyl, arylsulfonyl or a heterocyclic group or aryl substituted with carbamoyl or carbamoyl(lower)alkyl, each carbamoyl of which may be substituted with lower alkyl, arylsulfonyl or a heterocyclic group, $R_k^4$ is lower alkanoyl; lower alkyl substituted with carboxy, esterified carboxy or lower alkanoyl; or aryl substituted with carboxy, esterified carboxy or lower alkanoyl;

$R_l^4$ is lower alkyl substituted with hydroxy, or aryl substituted with hydroxy(lower)alkyl, $R_m^4$ is lower alkyl substituted with halogen, lower alkylsulfonyloxy or arylsulfonyloxy, or aryl substituted with halo(lower)alkyl, $A_a$ is lower alkylene, $Z^2$ is acid residue, $R_n^4$ is aryl optionally substituted with acyl or lower alkyl optionally substituted with acyl, $R_o^4$ is acyl, $R^6$ is hydrogen or lower alkyl, $R^7$ is hydrogen or lower alkyl, $R^8$ is acyl, $R_p^4$ is lower alkoxycarbonyl, $R^9$ is lower alkyl, $Z^3$ is acid residue, $R_q^4$ is formyl or lower alkyl substituted with formyl, and $R_r^4$ is lower alkyl substituted with substituent(s) selected from the group consisting of lower alkylthio, acyl (lower)alkylthio and heterocyclic(lower)alkylthio.

In the above and subsequent description of the present specification, suitable examples of the various definitions to be included within the scope of the invention are explained in detail in the following.

The term "lower" is intended to mean a group having 1 to 6 carbon atom(s), unless otherwise provided.

Suitable "lower alkyl" and lower alkyl moiety in the terms "acyl(lower)alkylthio", "halo(lower)alkyl", "cyano(lower) alkyl", "heterocyclic(lower)alkyl", "tetrazolyl(lower)alkyl", "lower alkylthio", "heterocyclic(lower)alkylthio", "esterified carboxy(lower)-alkylthio", "lower alkylcarbamoyl (lower)alkylthio", "carboxy(lower)alkylthio" "lower alkylamino", "lower alkyl (acyl) amino", "carbamoyl (lower)alkyl", "hydroxy (lower) alkyl" "acyl(lower)alkyl" "lower alkyl-sulfonyl" and "lower alkylsulfonyloxy" may be straight or branched one such as methyl, ethyl, propyl, isopropyl, butyl, isobutyl, tert-butyl, pentyl, hexyl or the like, in which preferable one is $C_1$–$C_4$ lower alkyl such as methyl, ethyl, propyl, isobutyl or tert-butyl.

Suitable "aryl" and aryl moiety in the terms "arylsulfonyl" and "arylsulfonyloxy" may be phenyl, naphthyl, phenyl substituted with lower alkyl [e.g. tolyl, xylyl, mesityl, cumenyl, di(tert-butyl)phenyl, etc.] and the like, in which preferable one is phenyl or tolyl.

Suitable "halogen" may be fluorine, chlorine, bromine and iodine, in which preferable one is chlorine.

Suitable "lower alkoxy" may be methoxy, ethoxy, propoxy, isopropoxy, butoxy and the like.

Suitable "lower alkylamino" may be mono or di(lower alkyl)amino such as methylamino, ethylamino, propylamino, isopropylamino, butylamino, tert-butylamino, isobutylamino, pentylamino, hexylamino, dimethylamino, diethylamino, dipropylamino, dibutylamino, diisopropylamino, dipentylamino, dihexylamino, N-methylethylamino or the like, in which preferable one is tert-butylamino.

Suitable lower alkylamino moiety in the term "lower alkyl(acyl)amino" may be one mentioned-above as mono (lower alkyl) amino.

Suitable "cyclo ( lower ) alkyl" may be cyclopropyl, cyclobutyl, cyclopentyl and cyclohexyl, in which preferable one is cyclopropyl or cyclobutyl.

Suitable "tricycloalkyl" may be ($C_7$–$C_{12}$)tricycloalkyl, in which preferable one is adamantly.

Suitable "lower alkylene" may be a straight or branched one such as methylene, ethylene, trimethylene, propylene, tetramethylene, pentamethylene, hexamethylene, ethylethylene or the like.

Suitable "lower alkenylene" may be a straight or branched one such as vinylene, propenylene, pentenylene, butenylene or the like.

Suitable "acid residue" may be halogen [e.g. fluoro, chloro, bromo, iodo], arenesulfonyloxy [e.g. benzenesulfonyloxy, tosyloxy, etc.], alkanesulfonyloxy [e.g. mesyloxy, ethanesulfonyloxy, etc.], and the like, in which preferable one is halogen.

Suitable "heterocyclic group" and heterocyclic moiety in the terms "heterocyclic(lower)alkyl" and "heterocyclic (lower)alkylthio" may be one containing at least one hetero atom selected from nitrogen, sulfur and oxygen atom, and may include saturated or unsaturated, monocyclic or polycyclic heterocyclic group, and preferable heterocyclic group may be N-containing heterocyclic group such as unsaturated 3 to 6 membered heteromonocyclic group containing 1 to 4 nitrogen atoms, for example, pyrrolyl, pyrrolinyl, imidazolyl, pyrazolyl, pyridyl, pyrimidinyl, pyrazinyl, pyridazinyl, triazolyl [e.g. 4H-1,2,4-triazolyl, 1H-1,2,3-triazolyl, 2H-1,2,3-triazolyl, etc.], tetrazolyl [e.g. 1H-tetrazolyl, 2H-tetrazolyl, etc.], etc.;

saturated 3 to 6-membered heteromonocyclic group containing 1 to 4 nitrogen atoms [e.g. pyrrolidinyl, imidazolidinyl, piperidino, piperazinyl, etc.];

unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g. tetrazolo[1,5-b]pyridazinyl, etc.], etc.;

unsaturated 3 to 6-membered heteromonocyclic group containing an oxygen atom, for example, pyranyl, furyl, etc.;

unsaturated, 3 to 6-membered heteromonocyclic group containing 1 to 2 sulfur atoms, for example, thienyl, etc.;

unsaturated 3 to 6-membered heteromonocyclic group containing 1 to 2 oxygen atoms and 1 to 3 nitrogen atoms, for example, oxazolyl, isoxazolyl, oxadiazolyl [e.g. 1,2,4-oxadiazolyl, 1,3,4-oxadiazolyl, 1,2,5-oxadiazolyl, etc.], etc.;

saturated 3 to 6-membered heteromonocyclic group containing 1 to 2 oxygen atoms and 1 to 3 nitrogen atoms [e.g. morpholinyl, etc.];

unsaturated condensed heterocyclic group containing 1 to 2 oxygen atoms and 1 to 3 nitrogen atoms [e.g. benzoxazolyl, benzoxadiazolyl, etc.];

unsaturated 3 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl, etc.], etc.;

saturated 3 to 6-membered heteromonocyclic group containing 1 to 2 sulfur atoms and 1 to 3 nitrogen atoms [e.g., thiazolidinyl, etc.];

unsaturated condensed heterocyclic group containing 1 to 2 sulfur atoms and 1 to 3 nitrogen atoms [e.g., benzothiazolyl, benzothiadiazolyl, etc.] and the like.

Preferable one in said heterocyclic group is tetrazolyl.

Suitable "acyl" and acyl moiety in the terms "lower alkyl ( acyl ) amino", "acyl ( lower ) alkyl" and "acyl(lower)alkylthio" may be carboxy; esterified carboxy; carbamoyl optionally substituted with lower alkyl, substituted or unsubstituted arylsulfonyl, lower alkylsulfonyl or a heterocyclic group; lower alkanoyl; aroyl; a heterocycliccarbonyl and the like.

The esterified carboxy may be substituted or unsubstituted lower alkoxycarbonyl [e.g. methoxycarbonyl, ethoxycarbonyl, propoxycarbonyl, butoxycarbonyl, hexyloxycarbonyl, 2-iodoethoxycarbonyl, 2,2,2-trichloroethoxycarbonyl, etc.], substituted or unsubstituted aryloxycarbonyl [e.g. phenoxycarbonyl, 4-nitrophenoxycarbonyl, 2-naphthyloxycarbonyl, etc.], substituted or unsubstituted ar(lower)alkoxycarbonyl [e.g. benzyloxycarbonyl, phenethyloxycarbonyl, benzhydryloxycarbonyl, 4-nitrobenzyloxycarbonyl, etc.] and the like, in which preferable one is unsubstituted lower alkoxycarbonyl.

The carbamoyl substituted with lower alkyl may be methylcarbamoyl, ethylcarbamoyl, propylcarbamoyl, dimethylcarbamoyl, diethylcarbamoyl, N-methyl-N-ethylcarbamoyl and the like, in which preferable one is dimethylcarbamoyl.

The carbamoyl substituted with substituted or unsubstituted arylsulfonyl may be phenylsulfonylcarbamoyl, tolylsulfonylcarbamoyl, vinyloxyphenylsulfonylcarbamoyl and the like.

The carbamoyl substituted with lower alkylsulfonyl may be methylsulfonylcarbamoyl, ethylsulfonylcarbamoyl and the like.

The carbamoyl substituted with a heterocyclic group may be one substituted with a heterocyclic group as mentioned above, in which preferable one is tetrazolylcarbamoyl.

The lower alkanoyl may be substituted or unsubstituted one such as formyl, acetyl, propionyl, butyryl, isobutyryl, valeryl, isovaleryl, pivaloyl, hexanoyl, trifluoroacetyl, methoxycarbonylisovaleryl or the like, in which preferable one is methoxycarbonylisovaleryl, formyl or acetyl.

The aroyl may be benzoyl, naphthoyl, toluoyl, di(tert-butyl)benzoyl and the like.

The heterocyclic moiety in the term "a heterocycliccarbonyl" may be one mentioned above as a heterocyclic group.

The substituent (s) on lower alkyl for $R^4$ may be plural and in such case the substituents may be the same or different.

In the present invention, please note that the four substituents on

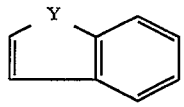

ring may substitute to any positions of said ring respectively.

Preferable compound (I) is one which has halogen for $R^1$ hydrogen for $R^2$ hydrogen for $R^3$ hydrogen, nitro, lower alkanoyl, lower alkoxycarbonyl, carboxy, lower alkoxycarbonyl(lower)alkanoyl or lower alkyl which may be substituted with substituent(s) selected from the group consisting of hydroxy, carboxy, lower alkoxycarbonyl, tetrazolylcarbamoyl, lower(alkyl)carbamoyl, arylsulfonylcarbamoyl, carboxy(lower)alkylthio, lower alkylthio, tetrazolyl(lower)alkyl, lower alkoxycarbonyl(lower)alkylthio, lower alkylcarbamoyl(lower)alkylthio and aryl(more preferably phenyl) optionally substituted with halo(lower)alkyl, cyano(lower)alkyl, tetrazolyl(lower)alkyl, cyano, carboxy, lower alkoxycarbonyl, aryl(more preferably lower alkyl substituted phenyl)sulfonylcarbamoyl, tetrazolylcarbamoyl or tetrazolyl for $R^4$ hydrogen, hydroxy, lower alkyl or lower alkoxy for $R^5$ a single bond for A, a single bond, O or NH for X and O for Y.

More preferable compound (I) is one which has halogen for $R^1$ hydrogen for $R^2$ hydrogen for $R^3$ hydrogen lower alkanoyl, lower alkoxycarbonyl(lower)alkanoyl or lower alkyl which may be substituted with substituent(s) selected from the group consisting of hydroxy, carboxy, lower alkoxycarbonyl, tetrazolylcarbamoyl, lower(alkyl)carbamoyl, arylsulfonylcarbamoyl, carboxy(lower)alkylthio, lower alkylthio, tetrazolyl(lower)alkyl, lower alkoxycarbonyl(lower)alkylthio, lower alkylcarbamoyl(lower)alkylthio and aryl(more preferably phenyl) optionally substituted with halo(lower)alkyl, cyano(lower)alkyl, tetrazolyl(lower)alkyl, cyano, carboxy, lower alkoxycarbonyl, aryl(more preferably lower alkyl substituted phenyl)sulfonylcarbamoyl, tetrazolylcarbamoyl or tetrazolyl for $R^4$ hydrogen for $R^5$ a single bond for A, a single bond, O or NH for X and O for Y.

Most preferable compound (I) is one which has halogen for $R^1$ hydrogen for $R^2$ hydrogen for $R^3$ lower alkyl substituted with aryl(more preferably phenyl) which is substituted with tetrazolyl(lower)alkyl for $R^4$ hydrogen for $R^5$ a single bond for A, O for X and O for Y Suitable pharmaceutically acceptable salts of the object compound [I] are conventional non-toxic salts and include an acid addition salt such as an inorganic acid addition salt [e.g. hydrochloride, hydrobromide, sulfate, phosphate, etc.] and an organic acid addition salt [e.g. formate, acetate, trifluoroacetate, maleate, tartrate, methanesulfonate, benzenesulfonate, toluenesulfonate, etc.], a metal salt such as an alkali metal salt [e.g. sodium salt, potassium salt, etc.] and an alkaline earth metal salt [e.g. calcium salt, magnesium salt, etc.], and the like.

The processes for preparing the object compound (I) are explained in detail in the following.

Process 1

The object compound (Ia) or its salt can be prepared by subjecting a compound (II) or its salt to cyclization reaction.

Suitable salt of the compound (II) may be the same as those exemplified for the compound (I).

This reaction is preferably carried out in the presence of a dehydrating agent [e.g. acetic anhydride, etc.] or a base such as alkali metal [e.g. lithium, sodium, potassium, etc.], alkaline earth metal [e.g. calcium, magnesium, etc.], alkali metal hydride [e.g. sodium hydride, etc.], alkaline earth metal hydride [e.g. calcium hydride, etc.], alkali metal alkoxide [e.g. sodium methoxide, sodium ethoxide, potassium tert-butoxide, etc.], alkaline earth metal alkoxide [e.g. magnesium methoxide, magnesium ethoxide, etc.], trialkylamine [e.g. trimethylamine, triethylamine, etc.], picoline, 1,5-diazabicyclo[4.3.0]non-5-ene, 1,4-diazabicyclo[2.2.2] octane, 1,8-diazabicyclo[5.4.0]undec-7-ene, or the like.

The reaction is usually carried out in a conventional solvent such as dioxane, tetrahydrofuran, pyridine, aromatic hydrocarbon [e.g. benzene, toluene, xylene, etc.]or any other organic solvent which does not adversely influence the reaction.

The reaction temperature is not critical, and the reaction is usually carried out under cooling to hating.

In this reaction, in case that the compound (II) having hydrogen for $R^4$ and O for X is used as a starting compound, the compound (Ia) having acyl for $R^4$ and O for X may be obtained according to reaction conditions. This case is included within the scope of the present reaction.

Process 2

The object compound (Ic) or its salt can be prepared by subjecting a compound (Ib) or its salt to dealkylation or deacylation reaction.

Suitable salts of the compounds (Ib) and (Ic) may be the same as those exemplified for the compound (I).

The reaction is carried out in accordance with a conventional method such as hydrolysis, reduction or the like.

The hydrolysis is preferably carried out in the presence of a base, an acid including Lewis acid or tri(lower alkyl) silyliodide. Suitable base may include an inorganic base and an organic base such as an alkali metal [e.g. lithium, sodium, potassium, etc.], an alkaline earth metal [e.g. magnesium, calcium, etc.], the hydroxide or carbonate or bicarbonate thereof, trialkylamine [e.g. trimethylamine, triethylamine, etc.], picoline, 1,5-diazabicyclo[4.3.0]non-5-ene, 1,4-diazabicyclo[2.2.2]-octane, 1,8-diazabicyclo[5.4.0]undec-7-ene, or the like. Suitable acid may include an organic acid [e.g.-formic acid, acetic acid, propionic acid, trichloroacetic acid, trifluoroacetic acid, etc.], an inorganic acid [e.g. hydrochloric acid, hydrobromic acid, hydroiodic acid, sulfuric acid, etc.] and Lewis acid [e.g. boron tribromide, etc.]. Suitable tri(lower alkyl)silyliodide may be trimethylsilyliodide and the like.

The reaction is usually carried out in a solvent such as water, an alcohol [e.g. methanol, ethanol, etc.], methylene chloride, tetrahydrofuran, a mixture thereof or any other solvent which does not adversely influence the reaction. A liquid base or acid can be also used as the solvent.

The reaction temperature is not critical and the reaction is usually carried out under cooling to heating.

The reduction can be applied preferably for elimination of methyl substituted with substituted- or unsubstituted-aryl.

This reduction method is usually carried out in a catalyst.

Suitable catalysts to be used in catalytic reduction are conventional ones such as platinum catalyst [e.g. platinum plate, spongy platinum, platinum black, colloidal platinum, platinum oxide, platinum wire, etc.], palladium catalyst [e.g. spongy palladium, palladium black, palladium oxide, palladium on carbon, colloidal palladium, palladium on barium sulfate, palladium on barium carbonate, etc.], nickel catalyst [e.g. reduced nickel, nickel oxide, Raney nickel, etc.], cobalt catalyst [e.g. reduced cobalt, Raney cobalt, etc.], iron catalyst [e.g. reduced iron, Raney iron, etc.], copper catalyst [e.g. reduced copper, Raney copper, Ullman copper, etc.] or the like.

The reaction is usually carried out in a conventional solvent such as water, an alcohol [e.g. methanol, ethanol, propanol, etc.], N,N-dimethylformamide, diethyl ether, dioxane, tetrahydrofuran or any other organic Solvent Which does not adversely influence the reaction.

The reaction temperature of this reduction is not critical and the reaction is usually carried out under cooling to warming.

In this reaction, in case that the compound (Ib) having lower alkoxy for $R^3$ and/or lower alkoxy for $R^5$ is used as a starting compound, the compound (Ic) having hydroxy for $R^3$ and/or hydroxy for $R^5$ may be Obtained according to reaction conditions. This case is included within the scope of the present reaction.

Process 3

The object compound (Ie) or its salt can be prepared by reacting a compound (Id) or its salt with a compound Suitable salts of the compounds (Id) and (Ie) may be the same as those exemplified for the compound (I).

When the compound (III) having halogen for $Z^1$ is used in this reaction, the reaction is preferably carried out in the presence of a base such as alkali metal [e.g. lithium, sodium, potassium, etc.], the hydroxide or carbonate or bicarbonate thereof [e.g. sodium hydroxide, potassium hydroxide, potassium carbonate, potassium bicarbonate, etc.], alkaline earth metal [e.g. calcium, magnesium, etc.], alkali metal hydride [e.g. sodium hydride, etc.], alkaline earth metal hydride [e.g. calcium hydride, etc.], alkali metal alkoxide [e.g. sodium methoxide, sodium ethoxide, potassium tert-butoxide, etc.], alkaline earth metal alkoxide [e.g. magnesium methoxide, magnesium ethoxide, etc.] or the like, or alkali metal iodide [e.g. sodium iodide, potassium iodide, etc.] and said base.

This reaction is usually carried out in a conventional solvent such as tetrahydrofuran, dioxane, hexamethylphosphoric triamide, N,N-dimethylformamide, acetone, a mixture thereof, or any other solvent which does not adversely influence the reaction. Additionally, in case that the compound (III) is in liquid, it can also be used as a solvent.

The reaction temperature is not critical, and the reaction is usually carried out under cooling to heating.

In this reaction, in case that the compound (Id) having hydroxy for $R^3$ and/or hydroxy for $R^5$ is used as a starting compound, the compound (Ie) having lower alkoxy for $R^3$ and/or lower alkoxy for $R^5$ may be obtained according to reaction conditions. This case is included within the scope of the present reaction.

Process 4

The object compound (Ig) or its salt can be prepared by reacting a compound (If) or its salt with a cyanide compound.

Suitable salts of the compounds (If) and (Ig) may be the same as those exemplified for the compound (I).

Suitable cyanide compound may be a metallic cyanide such as alkali metal cyanide [e.g. sodium cyanide, potassium cyanide, etc.], cuprous cyanide or the like.

This .reaction is preferably carried out in the presence of alkali metal iodide [e.g. sodium iodide., potassium iodide, etc.], phase transfer catalyst [e.g. Adogen 464 (Trademark: Aldrich), etc.], and the like.

The reaction is usually carried out in a conventional solvent such as water, an alcohol [e.g. methanol, ethanol, etc.], aromatic or aliphatic hydrocarbon [e.g. benzene, toluene, xylene, n-heptane, etc.], pyridine, quinoline, N,N-dimethylformamide, a mixture thereof or any other solvent which does not adversely influence the reaction.

The reaction temperature is not critical, and the reaction is usually carried out under warming to heating.

Process 5

The object compound (Ii) or its salt can be prepared by reacting a compound (Ih) or its salt with an azide compound.

Suitable salts of the compounds (Ih) and (Ii) may be the same as those exemplified for the compound (I).

Suitable azide compound may be alkali metal azide [e.g. sodium azide, potassium azide, etc.], alkaline earth metal azide [e.g. calcium azide, etc.], aluminum azide, hydrogen azide and the like.

The reaction is preferably carried out in the presence of ammonium halide [e.g. ammonium chloride, ammonium bromide, etc.], lower alkylammonium halide [e.g. trimethylammonium chloride, triethylammonium chloride, etc.] and the like.

The reaction is usually carried out in a conventional solvent such as tetrahydrofuran, dioxane, N,N-dimethylformamide or any other organic solvent which does not adversely influence the reaction.

The reaction temperature is not critical, and the reaction can be carried out under warming to heating.

Process 6

The object compound (Ik) or its salt can be prepared by subjecting a compound (Ij) or its salt to deesterification reaction.

Suitable salts of the compounds (Ij) or (Ik) may be the same as those exemplified for the compound (I).

The reaction is carried out in accordance with a conventional method such as hydrolysis, reduction or the like.

The hydrolysis is preferably carried out in the presence of a base, an acid including Lewis acid or tri(lower alkyl) silyliodide. Suitable base may include inorganic base and an organic base such as an alkali metal [e.g. lithium, sodium, potassium, etc.], an alkaline earth metal [e.g. magnesium, calcium, etc.], the hydroxide or carbonate or bicarbonate thereof, trialkylamine [e.g. trimethylamine, triethylamine, etc.], picoline, 1,5-diazabicyclo[4.3.0]non-5-ene, 1,4-diazabicyclo[2.2.2]octane, 1,8-diazabicyclo[5.4.0]undec-7.-ene, or the like. Suitable acid may include an organic acid [e.g. formic acid, acetic acid, propionic acid, trichloroacetic acid, trifluoroacetic acid, etc.], an inorganic acid-[e.g. hydrochloric acid, hydrobromic acid, hydroiodic acid, sulfuric acid, etc.] and Lewis acid [e.g. boron tribromide, etc.]. Suitable tri(lower alkyl)silyliodide may be trimethylsilyliodide and the like.

The reaction is usually Carried out in a solvent such as water, an alcohol [e.g. methanol, ethanol, etc.], methylene chloride, tetrahydrofuran, a mixture thereof or any other solvent which does not adversely influence the reaction. A liquid base or acid can be also used as the solvent. The reaction temperature is not critical and the reaction is usually carried out under cooling to warming.

The reaction can be applied preferably for elimination of the ester moiety such as 4-nitrobenzyl, 2-iodoethyl, 2,2,2-trichloroethyl, or the like. The reduction method applicable for the elimination reaction may include chemical reduction and catalytic reduction. Suitable reducing agents to be used in chemical reduction are a combination of metal [e.g. tin, zinc, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalyst [e.g. platinum plate, spongy platinum, platinum black, colloidal platinum, platinum oxide, platinum wire, etc.], palladium catalyst [e.g. spongy palladium, palladium black, palladium oxide, palladium on carbon, colloidal palladium, palladium on barium sulfate, palladium on barium carbonate, etc.], nickel catalyst [e.g. reduced nickel, nickel oxide, Raney nickel, etc.], cobalt catalyst [e.g. reduced cobalt, Raney cobalt, etc.], iron catalyst [e.g. reduced iron, Raney iron, etc.], copper catalyst [e.g. reduced copper, Raney copper, Ullman copper, etc.] or the like.

The reduction is usually carried out in a conventional solvent which does not adversely influence the reaction such as water, an alcohol [e.g. methanol, ethanol, propanol, etc.], N,N-dimethylformamide, or a mixture thereof. Additionally, in case that the above-mentioned acids to be used in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, etc., or a mixture thereof.

The reaction temperature of this reduction is not critical and the reaction is usually carried out under cooling to warming.

Process 7

The object compound (Im) or its salt can be prepared by reacting a compound (II) or its reactive derivative at the carboxy group or a salt thereof with an amine.

Suitable salts of the compounds (II) and (Im) and its reactive derivative at the carboxy group may be the same as those exemplified for the compound (I).

Suitable amine may be ammonia, arenesulfonamide, amine substituted with lower alkyl or a heterocyclic group.

The arenesulfonamide may be benzenesulfonamide, methylbenzenesulfonamide, ethylbenzenesulfonamide, naphthalenesulfonamide and the like, in which preferable one is methylbenzenesulfonamide.

The amine substituted with lower alkyl may be mono or di(lower alkyl)amine such as methylamine, ethylamine, dimethylamine, diethylamine, N-methylethylamine, or the like.

The amine substituted with a heterocyclic group may be one substituted with a heterocyclic group as mentioned above such as aminothiazole, aminothiadiazole, aminotriazole, aminotetrazole or the like, in which preferable one is aminotetrazole.

Suitable reaction derivative at the carboxy group of the compound (II) may include an ester, an acid halide, an acid anhydride and the like. The suitable examples of the reactive derivatives may be an acid halide [e.g. acid chloride, acid bromide, etc.]; a symmetrical acid anhydride; a mixed acid anhydride with 1,1-carbonyl diimidazole or an acid such as aliphatic carboxylic acid [e.g..acetic acid, pivalic acid, etc.], substituted phosphoric acid [e.g. dialkylphosphoric acid, diphenylphosphoric acid, etc.];

an ester such as lower alkyl ester [e.g. methyl ester, ethyl ester, propyl ester, hexyl ester, etc.], substituted or unsubstituted ar(lower)alkyl ester [e.g. benzyl ester, benzhydryl ester, p-chlorobenzyl ester, etc.], substituted or unsubstituted aryl ester [e.g. phenyl ester, tolyl ester, 4-nitrophenyl ester, 2,4-dinitrophenyl ester, pentachlorophenyl ester, naphthyl ester, etc.], or an ester with N,N-dimethylhydroxylamine, N-hydroxysuccinimide, N-hydroxyphthalimide or 1-hydroxy-6-chloro-1H-benzotriazole, or the like.

The reaction is usually carried out in a conventional solvent such as water, acetone, dioxane, chloroform, methylene chloride, ethylene chloride, tetrahydrofuran, ethyl acetate, N,N-dimethylformamide, pyridine or any other organic solvent which does not adversely influence the reaction. Among these solvents, hydrophilic solvents may be used in a mixture with water.

When the compound (II) is used in a free acid form in the reaction, the reaction is preferably carried out in the presence of a conventional condensing agent such as N,N,-dicyclohexylcarbodiimide, N-cyclohexyl-N'-morpholinoethylcarbodiimide, N-ethyl-N'-(3-dimethylaminopropyl)-carbodiimide, thionyl chloride, oxalyl chloride, lower alkoxycarbonyl halide [e.g. ethyl chloroformate, isobutyl chloroformate, etc.], 1-(p-chlorobenzenesulfonyloxy)-6-chloro-1H-benzotriazole, or the like. The reaction is also preferably carried out in the presence of a conventional base such as triethylamine, pyridine, di(lower)alkylaminopyridine [e.g. 4-dimethylaminopyridine, etc.], sodium hydroxide or the like.

The reaction temperature is not critical, and the reaction can be carried out under cooling to heating.

Process 8

The object compound (Io) or its salt can be prepared by reacting a compound (In) or its salt with a reducing agent.

Suitable salts of the compounds (In) and (Io) may be the same as those exemplified for the compound (I).

Suitable reducing agent may be aluminum hydride compound [e.g. lithium aluminum hydride, lithium tri-t-butoxyaluminum hydride, etc.], borohydride compound [e.g. sodium borohydride, etc.], aluminum alkoxide [e.g. aluminum isopropoxide, etc.] and the like.

The reaction is usually carried out in a conventional solvent, such as water, an alcohol [e.g. methanol, ethanol, propanol, isopropanol, etc.], chloroform, diethyl ether, dioxane, or any other organic solvent which does not adversely influence the reaction, or a mixture thereof.

The reaction temperature is not critical, and the reaction is usually carried out under cooling to heating.

Process 9

The object compound (Ip) or its salt can be prepared by reacting a compound (Io) or its salt with a halogenating agent or a sulfonylating agent.

Suitable salts of the compounds (Io) and (Ip) may be the same as those exemplified for the compound (I).

Suitable halogenating agent may be phosphorus trihalide [e.g. phosphorus trichloride, phosphorus tribromide, etc.], phosphorus pentahalide [e.g. phosphorus pentachloride, etc.], thionyl halide [e.g. thionyl chloride, etc.] and the like.

Suitable sulfonylating agent may be lower alkanesulfonyl halide [e.g. methanesulfonyl chloride, ethanesulfonyl chloride, methanesulfonyl bromide, etc.], arenesulfonyl halide [e.g. benzenesulfonyl chloride, toluenesulfonyl chloride, etc.] and the like.

The reaction is usually carried out in a conventional solvent such as carbontetrachloride, chloroform, methylene chloride, diethyl ether, tetrahydrofuran, dioxane or any other solvent which does not adversely influence the reaction.

The reaction temperature is not critical, and the reaction is usually carried out under cooling to heating.

Process 10

The object compound (Ir) or its salt can be prepared by reacting a compound (Iq) or its salt with a compound (IV) or its salt.

Suitable salts of the compounds (Iq) and (Ir) may an acid addition salt as exemplified for the compound Suitable salt of the compound (IV) may be a metal salt as exemplified for the compound (I).

This reaction can be carried out in substantially the same manner as Process 3, and therefore the reaction mode and-reaction condition (e.g. solvent, reaction temperature, etc.) of this reaction are to be referred to those as explained in Process 3.

Process 11

The compound (It) or its salt can be prepared by subjecting a compound (Is) or its salt to reduction.

Suitable salts of the compounds (Is) and (It) may be acid addition salts as exemplified for the compound (I).

The present reduction is carried out by chemical reduction, catalytic reduction, or the like.

Suitable reducing agents to be used in chemical reduction are a combination of metal [e.g. tin, zinc, iron, etc.] or metallic compound [e.g. stannous chloride, chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalyst [e.g. platinum plate, spongy platinum, platinum black, colloidal platinum, platinum oxide, platinum wire, etc.], palladium catalyst [e.g. spongy palladium, palladium black, palladium oxide, palladium on carbon, colloidal palladium, palladium on barium sulfate, palladium on barium carbonate, etc.], nickel catalyst [e.g. reduced nickel, nickel oxide, Raney nickel, etc.], cobalt catalyst [e.g. reduced cobalt, Raney cobalt, etc.], iron catalyst [e.g. reduced iron, Raney iron, etc.], copper catalyst [e.g. reduced copper, Raney copper, Ullman copper, etc.] or the like.

The reduction is usually carried out in a conventional solvent which does not adversely influence the reaction such as water, an alcohol [e.g. methanol, ethanol, propanol, etc.], N,N-dimethylformamide, or a mixture thereof. Additionally, in case that the above-mentioned acids to be used in chemical reduction are in liquid, they can also be used as a solvent. Further, a suitable solvent to be used in catalytic reduction may be the above-mentioned solvent and other conventional solvent such as diethyl ether, methylene chloride, dioxane, tetrahydrofuran, etc., or a mixture thereof.

The reaction temperature of this reduction is not critical and the reaction is usually carried out under cooling to warming.

Process 12

The object compound (Iu) or its salt can be prepared by reacting a compound (Id) or its salt with an acylating agent.

Suitable salts of the compounds (Id) and (Iu) may be the same as those exemplified for the compound (I).

The acylating agent may include an organic acid represented by the formula: $R_o^4$—OH, in which $R_o^4$ is acyl as illustrated above, or its reactive derivative.

The suitable reactive derivative of organic acid may be a conventional one such as an acid halide [e.g. acid chloride, acid bromide, etc.], an acid azide, an acid anhydride containing intramolecular and intermolecular ones, an activated amide, an activated ester or the like.

When free acid is used as an acylating agent, the acylation reaction may preferably be conducted in the presence of a conventional condensing agent such as N N'-dicyclohexylcarbodiimide or the like.

The reaction is usually carried out in a conventional solvent such as water, acetone, dioxane, chloroform, methylene chloride, acetonitrile, ethylene chloride, tetrahydrofuran, ethyl acetate, N,N-dimethylformamide, pyridine or any other organic solvent which does not adversely influence the reaction, or a mixture thereof.

The reaction is also preferably carried out in the presence of a conventional base such as triethylamine, pyridine, sodium hydroxide or the like.

The reaction temperature is not critical, and the reaction can be carried out under cooling to heating.

Process 13

The object compound (Iw) or its salt can be prepared by reacting a compound (iv) or its salt with a mixture of a compound (V) and a base.

Suitable salts of the compounds (Iv) and (Iw) may be the same as those exemplified for the compound (I).

Suitable base may be alkali metal [e.g. lithium, sodium, potassium, etc.], alkaline earth metal [e.g. calcium, magnesium etc.], alkali metal hydride [e.g. sodium hydride, etc.], alkaline earth metal hydride [e.g. calcium hydride, etc.], lower alkyl alkali metal [e.g. n-butyl lithium, etc.], alkali metal lower alkylamide [e.g. lithium diisopropylamide, etc.] and the like.

When a base is lower alkyl alkali metal or alkali metal lower alkylamide, it is preferable to add hexamethylphosphoric triamide into a mixture of lower alkyl substituted with esterified carboxy and a base.

The reaction is usually carried out in a conventional solvent such as diethyl ether, tetrahydrofuran, n-hexane, a mixture thereof, or any other solvent which does not adversely influence the reaction.

The reaction is also preferably carried out in the presence of trialkylhalosilane [e.g. trimethylchlorosilane, etc.].

The reaction temperature is not critical, and the reaction is usually carried out under cooling to warming.

Process 14

The object compound (Ix) or its salt can be prepared by reacting a compound (Iq) or its salt with a mixture of a compound (V) and a base.

Suitable salts of the compound (Iq) and (Ix) may be the same as those exemplified for the compound (I).

This reaction can be carried out in substantially the same manner as Process 13, and therefore the reaction mode and reaction condition (e.g. solvent, reaction temperature, etc.) of this reaction are to be referred to those as explained in Process 13.

Process 15

The object compound (I) or its salt can be prepared by reacting a compound (VI) or its salt with a compound (VII) or its salt in the presence of a condensing agent.

Suitable salt of the compound (VI) may be an acid addition salt as exemplified for the compound (I).

Suitable salt of the compound (VII) may be the same as those exemplified for the compound (I).

Suitable condensing agent may be benzenesulfonic acid, p-toluenesulfonic acid, naphthalenesulfonic acid and the like.

The reaction is usually carried out in a conventional solvent such as tetrahydrofuran, dioxane or any other solvent which does not adversely influence the reaction. Additionally, in case that the condensing agent is in liquid, it can also be used as a solvent.

The reaction temperature is not critical, and the reaction is usually carried out under warming to heating.

Process 16

The object compound (Iz) or its salt can be prepared by subjecting a compound (Iy) or its salt to oxidation reaction.

Suitable salts of the compounds (Iy) and (Iz) may be the same as those exemplified for the compound (I).

Suitable oxidizing agent used in this reaction may be manganese dioxide and the like.

The reaction is usually carried out in a conventional solvent such as pentane, hexane, benzene, diethyl ether, acetone, chloroform, dichloromethane or any other solvent which does not adversely influence the reaction.

The reaction temperature is not critical, and the reaction is usually carried out under cooling to heating.

Process 17

The object compound (I-1) or its salt can be prepared by subjecting a compound (Iz) or its salt to oxidation reaction in the presence of a cyanide compound and an alcohol.

Suitable salts of the compounds (Iz) and (I-1) may be the same as those exemplified for the compound (I).

Suitable oxidizing agent used in this reaction may be manganese dioxide and the like.

Suitable cyanide compound may be alkali metal cyanide [e.g. sodium cyanide, potassium cyanide, etc.] and the like.

Suitable alcohol may be lower alkanol [e.g. methanol, ethanol, etc.].

The reaction is also preferably carried out in the presence of an acid [e.g. acetic acid, etc.].

The reaction temperature is not critical, and the reaction is usually carried out under cooling to heating.

Process 18

The object compound (I-3) or its salt can be prepared by reacting a compound (I-2) or its salt with a compound Suitable salts of the compounds (I-2) and (I-3) may be the same as those exemplified for the compound (I).

This reaction can be carried out in substantially the same manner as Process B, and therefore the reaction mode and reaction condition (e.g. solvent, reaction temperature, etc.) of this reaction are to be referred to those as explained in Process 3.

In this reaction, in case that the compound (I-2) having hydroxy for $R^3$ and/or O, NH or S for X and hydrogen for $R^4$ is used as a starting compound, the Compound (I-3) having lower alkoxy for $R^3$ and/or O, NH or S for X and lower alkyl for $R^4$ may be obtained according to reaction conditions. This case is included within the scope of the present reaction.

Process 19

The object compound (I-5) or its salt can be prepared by reacting a compound (I-4) or its salt with a thiol compound.

Suitable salts of the Compounds (I-4) and (I-5) may be the same as those exemplified for the compound (I).

Suitable thiol compound may be lower alkylthiol, acyl (lower)alkylthiol, heterocyclic(lower)alkylthiol and the like.

The lower alkylthiol may be ethanethiol, 1-propanethiol, 1-butanethiol, 1-pentanethiol and the like.

The acyl(lower)alkylthiol may be mercapto(lower) alkanoic acid [e.g. mercaptoacetic acid, mercaptopropionic acid, mercaptobutyric acid, mercaptovaleric acid, etc.]; mercapto(lower)alkanoic acid ester [e.g. methyl mercaptoacetate, ethyl mercaptoacetate, methyl mercaptopropionate, ethyl mercaptopropionate, methyl mercaptobutyrate, ethyl mercaptovalerate, etc.]; mercapto (lower)alkanamide optionally substituted with lower alkyl, arylsulfoffyl or a heterocyclic group [e.g. mercaptoacetamide, mercaptopropionamide, N,N-dimethyl-mercaptopropionamide, etc.]; a mixture thereof; and the like.

The heterocyclic(lower)alkylthiol may be tetrazolylmethanethiol, tetrazolylethanethiol and the like.

This reaction is carried out in the presence of boron trihalide.[e.g. boron trifluoride, boron trichloride, etc.] or its diethyl ether complex.

The reaction is usually carried out in a conventional solvent such as acetonitrile, dioxane, chloroform, methylene chloride, tetrahydrofuran or any other solvent which does not adversely influence the reaction.

The reaction temperature is not critical, and the reaction is usually carried out under cooling.

In this reaction, in case that a mixture of two kind of a thiol compound is used, the compound (I-5) having different lower alkylthio, acyl(lower)alkylthio or heterocyclic(lower) alkylthio, lower alkylthio and acyl(lower)alkylthio, lower alkylthio and heterocyclic(lower)alkyl, or acyl(lower) alkylthio and heterocyclic(lower)alkylthio in lower alkyl substituted with substituent(s) selected from the group consisting of lower alkylthio, acyl(lower)alkylthio and heterocyclic(lower)alkylthio for $R_r^4$ may be obtained according to reaction conditions. This case is included within the scope of the present reaction.

The starting compounds (II) and (VIIa) or salts thereof can be prepared by the following processes.

Process A (IX) or its salt (X) or its salt (II) or its salt

Process B (XI) or its salt (Xa) or its salt

Process C (XII) or its salt (XIV) or its salt

Process D (XIV) or its salt (VIIa) or its salt wherein
$R^1$, $R^2$, $R^3$, $R^4$, $R^4$, $R^5$, A, X, $X_b$, Y and $Z^1$ are each as defined above,
$Z^4$ is acid residue,
$R_s^4$ is acyl, and
$Z^5$ is acid residue.

The above-mentioned processes for preparing the starting compounds are explained in detail in the following.

Process A

The compound (II) or its salt can be prepared by reacting a compound (IX) or its salt with a compound (X) or its salt.

Suitable salts of the compounds (II) and (X) may be the same as those exemplified for the compound (I).

Suitable salt of the compound (IX) may be the same as an acid addition salt exemplified for the compound (I).

This reaction can be carried out in substantially the same manner as Process 3, and therefore the reaction mode and reaction condition [e.g. solvent, reaction temperature, etc.] of this reaction are to be referred to those explained in Process 3.

Process B

The compound (Xa) or its salt can be prepared by reacting a compound (XI) or its salt with a compound Suitable salts of the compounds (Xa) and (XI) may be the same as those exemplified for the compound (I).

This reaction can be carried out in substantially the same manner as Process 3, and therefore the reaction mode and reaction condition [e.g. solvent, reaction temperature, etc.] of this reaction are to be referred to those explained in Process 3.

Process C

The compound (XIV) or its salt can be prepared by reacting a compound (XII) or its salt with a compound (XIII).

Suitable salts of the compounds (XII) and (XIV) may be the same as a metal salt exemplified for the compound (I).

This reaction can be carried out in substantially the same manner as Process 3., and therefore the reaction mode and reaction condition [e.g. solvent, reaction temperature, etc.] of this reaction are to be referred to those explained in Process 3.

Process D

The compound (VIIa) or its salt can be prepared by subjecting a compound (XIV) or its salt to cyclization reaction.

Suitable salts of the compounds (VIIa) and (XIV) may be the same as those exemplified for the compound (I).

This reaction can be carried out in substantially the same manner as Process 1, and therefore the reaction mode and reaction condition [e.g. solvent, reaction temperature, etc.] of this reaction are to be referred to those explained in Process 1.

The compounds obtained by the above processes can be isolated and purified by a conventional method such as pulverization, recrystallization, column chromatography, reprecipitation or the like, and converted to the desired salt in conventional manners, if necessary.

It is to be noted that the compound (I) and the other compounds may include one or more stereoisomers due to asymmetric carbon atoms, and all of such isomers and mixture thereof are included within the scope of this invention.

The object compound (I) or its pharmaceutically acceptable salts thereof possess strong activities as leukotriene and SRS-A antagonists or inhibitors, and are useful for the treatment and/or prevention of allergy or inflammation in human beings or animals, and more particularly to methods for prevention and/or treatment of asthma, psoriasis, hepatitis, pancreatitis, arthritis, nephritis, inflammatory bowel disease, septic shock, arteriosclerosis, myocardial infarction, cerebral vasospasm, rhinitis, conjunctivitis, dermatitis, rheumatism, peptic ulcer, gout and the like.

In order to illustrate the usefulness of the object compound (I), the pharmacological test data of a representative compound of the compound (I) is shown in the following.

$^3$-Leukotriene $D_4$ receptor binding

Test Method:

(a) Crude lung membrane preparation

Male Hartly strain guinea pigs were sacrificed by decapitation. The trachea and lung were removed and homogenized buffer (0.25M sucrose, 10 mM Tris-HCl pH 7.5, 0.1 mM EDTA) by using Polytoron (Kinematica). The homogenate was centrifuged (1000 xg, 10 min) to remove tissue clumps and the supernatant was centrifuged (14000 xg, 20 min) to yield pellets. The pellets were resuspended in buffer (5 mM Tris-HCl pH 7.5), homogenized with a teflon homogenizer and centrifuged (14000 xg, 20 min) to yield pellets which were referred to as crude membrane fractions. The obtained pellets were stored at −70° C. until use.

(b) $^3$H-Leukotriene $D_4$ binding to preparation membrane

Frozen crude membrane fractions were thawed and resuspended in Medium 1 (10 mM Tris-HCl pH 7.5, 10 mM $CaCl_2$, 10 mM $MgCl_2$, 5 mM cysteine, 5 mM glycine). In binding assays, $^3$H-Leukotriene $D_4$ (0.3 nM) and drug were incubated with 100 μl of the membrane preparation in Medium 1 at 25° C. for 30 minutes in a final volume of 500 μl. Separation of receptor-bound from free $^3$H-Leukotriene $D_4$ is achieved by immediate filtration through Whatman GF/B filters under vacuum and washed three times with 5 ml of ice-cold buffer (10 mM Tris-HCl pH 7.5). Non-specific binding was defined as binding in the presence of 1 μM Leukotriene $D_4$. The radioactivity retained on rinsed filters was determined by a liquid-scintillation counter (Packerd TRI-CARB 4530).

(ii) Test Result

| Test Compound (Example No.) | Dose (μg/ml) | Inhibition (%) |
|---|---|---|
| 7 | 1 | 97.5 |
| 8-1) | 1 | 98.9 |
| 42 | 1 | 100 |
| 46-3) | 1 | 100 |

For therapeutic purpose, the compound (I) and a pharmaceutically acceptable salt thereof of the present invention can be used in a form of pharmaceutical preparation containing one of said compounds, as an active ingredient, in admixture with a pharmaceutically acceptable carrier such as an organic or inorganic solid, semi-solid or liquid excipient suitable for oral, parenteral or external (topical) administration. The pharmaceutical preparations may be capsules, tablets, dragees, granules, suppositories, solution, lotion, inhalant, ophthalmic preparations, collunarium, suspension, emulsion, ointment, gel, or the like. If desired, there may be included in these preparations, auxiliary substances, stabilizing agents, wetting or emulsifying agents, buffers and other commonly used additives.

While the dosage of the compound (I) will vary depending upon the age and condition of the patient, an average single dose of about 0.1 mg, 1 mg, 10 mg, 50 mg, 100 mg, 250 mg, 500 mg and 1000 mg of the compound (I) may be effective for treating the above-mentioned diseases. In general, amounts between 0.1 mg/body and about 1,000 mg/body may be administered per day.

The following Preparations and Examples are given for the purpose of illustrating this invention.

Preparation 1

A mixture of 7-chloro-2-chloromethylquinoline (13.6 g), 2,5-dihydroxybenzaldehyde (10.6 g), potassium carbonate (10.6 g) and potassium iodide (1.0 g) in N,N-dimethylformamide was stirred at 57° C. for 2 hours under nitrogen atmosphere. After being cooled, the reaction mixture was poured into ice-water (1 l) and then adjusted to pH 7 with diluted aqueous hydrochloric acid. The resulting precipitates were collected by filtration, washed with water, and dried in vacuo to give 5-hydroxy-2-[2-(7-chloroquinolyl)]methoxybenzaldehyde (19.8 g).

Preparation 2

The following compounds were obtained according to a similar manner to that of Preparation 1.

1) 7-Chloro-2-(2,4-diformylphenoxymethyl)quinoline

IR (Nujol): 1695, 1610 $cm^{-1}$

NMR (DMSO-$d_6$, δ): 5.69 (2H, S), 7.55 (1H, d, J=8.7 Hz), 7.68 (1H, d, J=8.6 Hz), 7.88 (1H, d, J=B.6 Hz), 8.07 (1H, s), 8.12 (1H, s), 8.18 (1H, d, J=8.7 Hz), 8.29 (1H, s), 8.53 (1H, d, J=B.7 Hz), 8.98 (1H, s), 10.54 (1H, s)

2) 2-(2 4-Diformylphenoxymethyl)quinoline

IR (Nujol): 1680, 1600 $cm^{-1}$

NMR (CDCl$_3$, δ): 5.61 (2H, s), 7.28 (1H, d, J=8.7 Hz), 7.60 (1H, t, J=6.9 Hz), 7.65 (1H, d, J=8.5 Hz), 7.79 (1H, ddd, J=8.2, 6.9, 0.2 Hz), 7.89 (1H, d, J=8.2 Hz), 8.08 (1H, dd, J=8.7, 2.2 Hz), 8.09 (1H, d, J=6.9 Hz), 8.26 (1H, d, J=8.5 Hz), 8.38 (1H, d, J=2.2 Hz), 9.95 (1H, s), 10.65 (1H, s)

MASS (m/z): 291 (M$^+$)

3) 7-Chloro-2-(2,6-diformylphenoxymethyl)quinoline

IR (Nujol): 1690, 1620 $cm^{-1}$

NMR (CDCl$_3$, δ): 5.46 (2H, s), 7.45 (1H, t, J=7.7 Hz), 7.54 (1H, dd, J=8.7, 2.0 Hz), 7.69 (1H, d, J=8.5 Hz), 7.80 (1H, d, J=S.7 Hz), 8.05 (1H, d, J=2.0 Hz), 8.15 (2H, d, J=7.7 Hz), 8.25 (1H, d, J=8.5 Hz), 10.45 (2H, s)

MASS (m/z): 325 (M⁺)

4) 2-Hydroxy-4-(3-ethoxycarbonyl)propoxybenzaldehyde

IR (Film): 1730, 1640, 1575 cm⁻¹

NMR (CDCl₃, δ): 1.27 (3H, t, J=7.2 Hz), 2.13 (2H, tt, J=7.2, 6.1 Hz), 2.51 (2H, t, J=7.2 Hz), 4.07 (2H, t, J=6.1 Hz), 4.15 (2H, q, J=7.2 Hz), 6.41 (1H, d, J=2.3 Hz), 6.52 (1H, dd, J=8.6, 2.3 Hz), 7.42 1H, d, J=S.6 Hz), 9.71 (1H, s), 11.46 (1H, s)

MASS (m/z): 255 (M⁺), 207

5) 7-Chloro-2-[2-formyl-5-(3-ethoxycarbonylpropoxy) phenoxymethyl]quinoline

NMR (CDCl₃, δ): 1.25 (3H, t, J=7.1 Hz), 2.10 (2H, tt, J=7.2, 6.2 Hz), 2.49 (2H, t, J=7.2 Hz), 4.03 (2H, t, J=6.2 Hz), 4.14 (2H, q, J=7.1 Hz), 5.45 (2H, s), 6.56 (1H, d, J=2.1 Hz), 6.57 (1H, J=8.6, 2.1 Hz], 7.53 (1H, dd, J=8.7, 2.0 Hz),7.70 (1H, d, J=8.5 Hz), 7.79 (1H, d, J=8.7 Hz), 7.84 (1H, d, J=8.6 Hz), 8.08 (1H, d, J=2.0 Hz), 8.22 (1H, d, J=8.5 Hz), 10.45 (1H, s)

6) 7-Chloro-2-[2-formyl-5-(2-methoxycarbonyl-2-methylpropoxy)phenoxymethyl]quinoline NMR (CDCl₃, δ): 1.31 (6B, s), 3.69 (3H, s) , 3.99 (2H, s), 5.46 (2H, s), 6.58 (1H, dd, J=8.6, 2.1 Hz), 6.63 (1H, d, J=2.1 Hz), 7.53 (1H, dd, J=8.7, 2.0 Hz), 7.72 (1H, d, J=S.5 Hz), 7.80 (1H, d, J=S.7 Hz), 7.83 (1H, d, J=8.6 Hz), 8.09 (1H, d, J=2.0 Hz), 8.23 (1H, d, J=8.5 Hz), 10.24 (1H, s)

=MASS (m/z): 427 (M⁺)

7) 2-Hydroxy-5-[3-ethoxycarbonyl)propoxybenzaldehyde

NMR (CDCl₃, δ): 1.27 (3B, t, J=7.1 Hz), 2.12 (2H, tt, J=7.2, 6.1 Hz), 2.52 (2B, t, J=7.2 Hz), 4.01 (2H, t, J=6.1 Hz), 4.16 (2H, q, J=7.1 Hz), 6.93 (1H, d, J=9.0 Hz), 7.01 (1H, d, J=3.0 Hz), 7.14 (1H, dd, J=9.0, 3.0 Hz), 9.85 (1H, s), 10.65 (1H, s)

8) 5-Acetyl-2-(methoxycarbonyl)methoxybenzaldehyde

NMR (CDCl₃, δ): 2.61 (3H, s), 3.84 (3H,¹ s), 4.8 12H, s), 6.94 (1H, d, J=8.8 Hz), 8.21 (1H, dd, J=8.8, 2.4 Hz), 8.44 (1H, d, J=2.4 Hz), 10.56 (1H, s)

9) 7-Chloro-2-(2-formyl -4-nitrophenoxymethyl)quinoline.

IR (Nujol): 1685, 1610, 1520, 1345 cm⁻¹

NMR [DMSO-d₆, δ): 5.27 (2H, s), 7.57 (1H, d, J=8.9 Hz), 7.67 (1H, dd, J=2.2, 8.7 Hz), 7.78 d, J=8.7 Hz), 8.05 (1H, d, J=2.2 Hz), 8.08 (1H, d, J=8.9 Hz), 8.4–8.6 (3H, m), 10.49 (1H, s)

MASS (m/z): 342 (M⁺), 313, 177 (base)

10) Methyl 3-acetyl-4-[2-(7-chloroquinoyl)methoxy]-benzoate mp: 123°–124° C.

IR (Nujol): 1720, 1680, 1600, 1500 cm⁻¹

NMR (DMSO-d₆, δ): 2.65 (3H, s), 3.85 (3H, s), 5.62 (2H, s), 7.42 (1H, d, J=8.8 Hz), 7.68 (1H, dd, J=2.1, 8.8 Hz), 7.86 (1H, d, J=8.5 Hz), 8.0–8.1 (3H, m), 8.22 (1H, d, J=2.2 Hz), 8.51 (1H, d, J=8.5 Hz)

MASS (m/z): 369 (M⁺), 351 , 326, 192, 176 (base)

11) 7-Chloro-2-[2,4-bis(methoxycarbonyl)phenoxymethyl]-quinoline mp: 190°–191° C.

IR (Nujol): 1723, 1713, 1615, 1500 cm⁻¹

NMR (DMSO-d₆, δ): 3.85 (3H, s), 3.87 (3H, s), 5.57 (2H, s), 7.44 (1H, d, J=8.7 Hz), 7.67 (1H, dd, J=8.7, 2.2 Hz), 7.87 (1H, d, J=8.7 Hz), 8.10–8.15 (1H, m), 8.13 (1H, dd, J=2.2, 8.7 Hz), 8.31 (1H, s), 8.36 (1H, d, J=2.2 Hz), 8.54 (1H, d, J=8.7 Hz)

MASS (m/z): 385 (M⁺), 353, 326, 176 (base)

Preparation 3

To a mixture of 5-acetyl-2-(methoxycarbonyl) methoxybenzaldehyde (4.47 g) in toluene, a solution of 1,8-diazabicyclo[5.4.0]-7-undecene (1.30 g) in toluene (8 ml) was added dropwise for 15 hours at refluxing temperature. After being cooled, the resulting mixture was washed with water, dried lover magnesium sulfate and concentrated under reduced pressure. The resulting precipitates were washed with diethyl ether to give 5-acetyl-2-methoxycarbonylbenzofuran (1.65 g).

NMR (CDCl₃, δ): 2.68 (3H, s), 4.00 (3H, s), 7.60 (1H, s), 7.64 (1H, d, J=8.8 Hz), 8.11 (1H, dd, J=8.8, 1.8 Hz), 8.34 (1H, d, J=1.8 Hz)

EXAMPLE 1

A mixture of 5-hydroxy-2-[2-(7-chloroquinolyl)]-methoxybenzaldehyde (19.8 g) and acetic anhydride (48 ml) in toluene (198 ml) was refluxed for 5 hours. After being cooled, the resulting precipitates were collected by filtration and washed with toluene to give 7-chloro-2-(5-acetoxybenzofuran-2-yl)quinoline (15.13 g).

IR (Nujol) : 1760, 1610, 1600 cm⁻¹

NMR (CF₃COOD, δ): 2.50 (3H, s), 7.3–8.5 (8H, m), 9.0 (1H, d, J=9 Hz)

EXAMPLE 2

To a suspension of 7-chloro-2-(5-acetoxybenzofuran-2-yl)quinoline (16.7 g) in methanol (400 ml), 1N aqueous sodium hydroxide (50 ml) was added at ambient temperature. The mixture was stirred for 1 day. After the solvent was removed under reduced pressure, the residue was suspended with water, and adjusted to pH 6–7 with diluted aqueous hydrochloric acid. After the resulting suspension was stirred at ambient temperature for 1 hour, the precipitates were collected by filtration, washed with water and dried in vacuo to give crude material (15 g). The crude material was dissolved in N,N-dimethylformamide (200 ml) at 80° C., and the resulting solution was allowed to stand at ambient temperature. The resulting crystals were filtered off and washed with N,N-dimethylformamide. The filtrate was poured into Water (500 ml). The resulting precipitates were collected by filtration, washed with water and dried in vacuo to give 7-chloro-2-(5-hydroxybenzofuran-2-yl)quinoline (12.1 g).

mp: 276°–278° C. (dec.)

IR (Nujol): 1605, 1575 cm⁻¹

NMR (DMSO-d₆, δ): 6.90 (1H, dd, J=2.1, 8.7 Hz), 7.08 (1H, d, J=2.1 Hz), 7.54 (1H, d, J=8.7 Hz), 7.64 (1H, dd, J=2.1, 8.7 Hz), 7.72 (1H, d, J=0.9 Hz), 8.1–8.15 (3H, m), 8.52 (1H, d, J=8.7 Hz), 9.39 (1H, s)

MASS (m/z): 295 (M⁺)

EXAMPLE 3

To a cooled suspension of 7-chloro-2-(5-hydroxybenzofuran-2-yl)quinoline (0.71 g) in tetrahydrofuran (12 ml), sodium hydride (60% in mineral oil, 0.125 g) was added below 10° c. After being stirred for 15 minutes, α,α'-dichloro-o-xylene (1.68 g) was added to the mixture. After subsequently being stirred at ambient temperature for 1.5 hours, the mixture was refluxed for 25 hours. After the solvent was removed under reduced pressure, the residue was subjected to column chromatography on silica gel (25 g) and eluted with a mixture of chloroform and n-hexane (1:1). The fractions containing object compound were combined and concentrated under reduced pressure give 7-chloro-2-[5-(2-chloromethylbenzyloxy)benzofuran-2-yl]quinoline (0.56 g).

IR (Nujol): 1600, 1210 cm$^{-1}$

NMR (CDCl$_3$, δ): 4.77 (2H, s), 5.26 (2H, s), 7.07 (1H, dd, J=2.6, 8.7 Hz), 7.24 (1H, m), 7.35–7.53 (6H, m), 7.56 (1H, s), 7.74 (1H, d, J=8.7 Hz), 7.98 (1H, d, J=8.7 Hz), 8.17 (1H, d, J=3.2 Hz), 8.18 (1H, d, J=8.7 Hz)

MASS (m/z): 433 (M$^+$), 399, 295, 238, 139

EXAMPLE 4

The following compounds were obtained according to a similar manner to that of Example 3.

1) 7-Chloro-2-[5-(3-chloromethylbenzyloxy)benzofuran-2-yl]quinoline

IR (Nujol): 1600, 1580, 1210 cm$^{-1}$

NMR (CDCl$_3$, δ): 4.62 (2H, s), 5.12 (2H, s), 7.07 (1H, dd, J=2.6, 8.9 Hz), 7.18 (1H, d, J=2.5 Hz), 7.25–7.50 (6H, m), 7.53 (1H, s), 7.73 (1H, d, J=8.7 Hz), 7.97 (1H, d, J=8.7 Hz), 8.17 (1H, d, J=2.3 Hz), 8.19 (1H, d, J=8.7 Hz)

MASS (m/z): 433 (M$^+$), 399, 295, 266, 238

2) 7-Chloro-2-[5-(4-chloromethylbenzyloxy)benzofuran-2-yl]quinoline

IR (Nujol): 1600, 1580, 1210 cm$^{-1}$

NMR [CDCl$_{3, \delta n}$): 4.61 (2H, s), 5.12 (2H; s), 7.05 (1H, dd, J=2.4, 9.0 Hz),:7.17 (1H, d, J=2.4 Hz), (1H, d, J=8.7 Hz), 8.16 (1H, d, J=2.4 Hz), 8.18 7.31–7.6 (7H, m), 7.73 (1H, d, J=8.7 Hz), 7.97 (1H, d, J=8.7 Hz)

MASS (m/Z): 433 (M$^+$), 399, 295, 266, 238

3) 7-Chloro-2-[6-(2-chloromethylbenzyloxy)benzofuran-2-yl]quinoline

IR (Nujol): 5600, 1270, 1125 cm$^{-1}$

NMR (CDCl$_3$, δ): 4.76 (2H, s), 5.30 (2H, S), 7.02 (1H, dd, J=2.6, 8.7 Hz), 7.24 (1H, d, J=2.6 Hz) 7.36–7.60 (5H, m), 7.51 (1H, s), 7.58 (1H, d, J=8.7 Hz), 7.73 (1H, d, J=8.7 Hz), 7.94 (1H, d, J=8.7 Hz), 8.1–8.2 (2H, m)

MASS (m/z): 433 (M$^+$), 294 (base)

EXAMPLE 5

A mixture of 7-chloro-2-[5-(2-chloromethylbenzyloxy)-benzofuran-2-yl]quinoline (0.52 g), potassium cyanide (0.16 g) and Adogen 464 (Trademark Aldrich, one drop) in a mixture of toluene (6 ml) and water (6 ml) was refluxed for 4 hours. The organic layer was separated, dried over magnesium sulfate and concentrated under reduced pressure. The residue was subjected to column chromatography on silica gel and eluted with dichloromethane. The fractions containing object compound were combined and concentrated under reduced pressure to give 2-[2-[2-(7-chloroquinolyl)]benzofuran-5-yloxy]methylbenzyl cyanide (0.35 g).

IR (Nujol): 2360, 1600, 1210 cm$^{-1}$

NMR (CDCl$_3$, δ): 3.91 (2H, s), 5.13 (2H, s), 7.05 (1H, dd, J=2.6, 8.7 Hz), 7.23 (1H, d, J=2.6 Hz), 7.40–7.58 (7H, m), 7.75 (1H, d, J=8.7 Hz), 7.98 (1H, d, J=8.7 Hz), 8.19 (1H, s), 8.21 (1H, d, J=8.7 Hz)

MASS (m/z): 424 (M$^+$), 294, 238, 130

EXAMPLE 6

The following compounds were obtained according to a Similar manner to that of Example 5.

1) 3-[2-[2-(7-Chloroquinolyl)]benzofuran-5-yloxy]-methylbenzyl cyanide

IR (Nujol): 2360., 1600, 1210 cm$^{-1}$

NMR (DMSO-d$_6$, δ): 4.10 (2H, s), 5.19 (2H, s), 7.12 (1H, dd, J=2.6, 8.9 Hz), 7.3–7.5 (5H, m), 7.62–7.70 (2H, m), 7.78 (1H, s), 8.05 (1H, d, J=8.8 Hz), 8.12 (1H, d, J=2.2 Hz), 8.15 (1H, d, J=8.7 Hz), 8.53 (1H, d, J=8.7 Hz)

MASS (m/z): 424 (M$^+$), 294, 116

2) 4-[2-[2-(7-Chloroquinolyl)]benzofuran-5-yloxy]-methylbenzyl cyanide

IR (Nujol) : 1600, 1200 cm$^{-1}$

NMR (DMSO-d$_{6, \delta)}$: 4.06 (2H, s), 5.18 (2H, s), 7.11 (1H, dd, J=2.6, 9.0 Hz), 7.36 (1H, d, J=2.6 Hz), 7.39 (2H, d, J=8.5 Hz), 7.53 (2H, d, J=8.5 Hz), 7.65 (1H, dd, J=2.6, 8.7 Hz), 7.66 (1H, d, J=9.0 Hz), 7.87 (1H, s), 8.06 (1H, d, J=8.7 Hz), 8.10 (1H, d, J=2.6 Hz), 8.15 (1H, d, J=8.7 Hz), 8.53 (1H, d, J=8.7 Hz)

MASS (m/z): 424 (M$^+$), 295, 266, 238, 130

3) 2-[2-[2-(7-Chloroquinolyl)]benzofuran-5-yloxy]-methylbenzyl cyanide

IR (Nujol): 2250, 1620, 1600 cm$^{-1}$

NMR (DMSO-d$_6$, δ): 4.16 (2H, s), 5.30 (2H, s), 7.10 (1H, dd, J=2.2, 8.7 Hz), 7.40–7.66 (6H, m), 7.69 (1H, d, J=8.7 Hz), 7.82 (1H, s), 8.05 (1H, d, J=8.7 Hz), 8.11 (1H, d, J=2.2 Hz), 8.13 (1H, d, J=8.7 Hz), 8.52 (1H, d, J=8.6 Hz)

MASS (m/z.): 424 (M$^+$), 294 (base), 238

EXAMPLE 7

A mixture of 2-[2-[2-(7-chloroquinolyl)]benzofuran-5-yloxy]methylbenzylcyanide (0.2 g), sodium azide (0.28 g) and ammonium chloride (0.23 g) in N,N-dimethylformamide (2 ml) was stirred at 110° C. for 2 days. After being cooled, the mixture was poured into brine (10 ml) and the resulting precipitates were collected by filtration to give crude material. This material was subjected to column chromatography on silica gel and eluted with chloroform, successively with a mixture of chloroform and methanol (20:1). The fractions containing object compound were combined and concentrated under reduced pressure to give 5-[2-[2-[2-(7-chloroquinolyl)]benzofuran-5-yloxy]-methyl]benzyl-1H-tetrazole (0.05 g).

mp: 212°–214° C.

IR (Nujol): 2700, 1600, 1200 cm$^{-1}$

NMR (DMSO-d$_6$, δ): 4.43 (2H, s), 5.56 (2H, s), 7.05 (1H, dd, J=2.6, 8.7 Hz), 7.57–7.37 (4H, m), 7.56 (1H, m), 7.75 (1H, d, J=8.7 Hz), 7.76 (1H, d, J=8.7 Hz), 7.80 (1H, s), 8.08 (1H, d, J=8.7 Hz), 8.13 (1H, d, J=3.2 Hz), 8.16 (1H, d, J=8.7 Hz), 8.54 (1H, d, J=8.7 Hz)

MASS (m/z): 467 (M$^+$), 429, 295

EXAMPLE 8

The following compounds were obtained according to a similar manner to that of Example 7.

1) 5-[3-[2-[2-(7-Chloroquinolyl)]benzofuran-5-yloxy]-methylphenyl]-1H-tetrazole mp: 253°–254° C.

IR (Nujol) : 3450, 2600, 1600 cm$^{-1}$

NMR (DMSO-d$_6$, δ): 5.30 (2H, s), 7.17 (1H, dd, J=2.6, 8.9 Hz), 7.42 (1H, d, J=2.6 Hz), 7.6–7.74 (4H, m), 7.79 (1H, s), 8.00–8.51 (5H, m), 8.54 (1H, d, J=B.7 Hz)

FAB-MASS (m/z): 454 ((M+1)$^+$), 307, 289

2) 5-[3-[5-[2-(7-Chloroquinolyl)]benzofuran-5-yloxy]-methyl]benzyl-1H-tetrazole mp: 234°–236° C.

IR (Nujol): 2700, 2600, 1600 cm$^{-1}$

NMR (DMSO-d$_6$, δ): 4.34 (2H, s), 5.14 (2H, s), 7.10 (1H, dd, J=2.6, 8.9 Hz), 7.26 (1H, m), 7.36–7.41 (4H, m), 7.65 (1H, d, J=8.7 Hz), 7.66 (1H, d, J=8.8 Hz), 7.79 (1H, s), 8.08 (1H, d, J=8.7 Hz), 8.13 (1H, d, J=2.6 Hz), 8.16 (1H, d, J=8.9 Hz), 8.54 (1H, d, J=8.7 Hz)

FAB-MASS (m/z): 468 ((M+1)$^+$), 307, 289

3) 5-[4-[2-[2-[7-Chloroquinolyl)]benzofuran-5-yloxy]-methyl]benzyl-1H-tetrazole mp: 204°–206° C.

IR (Nujol): 2700, 2600, 1600 cm$^{-1}$

NMR (DMSO-d$_6$, δ): 4.31 (2H, s), 5.15 (2H, s), 7.10 (1H, dd, J=2.5, 9.0 Hz), 7.31 (2H, d, J=8.1 Hz), 7.36 (1H, d, J=2.5 Hz), 7.47 (2H, d, J=8.1 Hz), 7.65 (1H, dd, J=2.5, 8.7 Hz), 7.66 (1H, d, J=9.0 Hz), 7.78 (1H, s), 8.08 (1H, d, J=8.7 Hz), 8.13 (1H, d, J=2.5 Hz), 8.16 (1H, d, J=8.7 Hz), 8.54 (1H, d, J=8.7 Hz)

FAB-MASS (m/z): 468 ((M+1)$^+$), 307; 289

4) [2-[2-[2-(7-Chloroquinolyl)]benzofuran-5-yloxy]-methylphenyl]-1H-tetrazole mp: 232°–233° C.

IR (Nujol): 2700, 2600, 1590, 1380 cm$^{-1}$

NMR (DMSO-d$_6$, δ): 5.51 (2H, s), 6.99 (1H, d, J=2.1, 8.7 Hz), 7.02 (1H, d, J=2.6 Hz), 7.27–7.69 (4H, m), 7.78 (1H, s), 7.79 (1H, m), 7.87 (1H, dd, J=1.6, 7.6 Hz), 8.07 (1H, d, J=8.8 Hz), 8.12 d, J=2.1 Hz), 8.14 (1H, d, J=8.7 Hz), 8.53 (1H, d, J=8.7 Hz)

FAB-MASS (m/z): 454 ((M+1)$^+$), 307, 289

5) 5-[4-[2-[2-(7-Chloroquinolyl)]benzofuran-5-yloxy]-methylphenyl]-1H-tetrazole mp: 263°–264° C.

IR (Nujol): 3450, 2600, 1600 cm$^{-1}$

NMR (DMSO-d$_6$, δ): 5.23 (2H, s), 7.15 (1H, ad, J=2.6, 8.9 Hz), 7.40 (1H, d, J=2.5 Hz), 7.6–7.7 (4H, m), 7.79 (1H, s), 8.06 (1H, d, J=8.9 Hz), 8.07 (2H, d, J=8.7 Hz), 8.13 (1H, d, J=2.2 Hz), 8.16 (1H, d, J=8.7 Hz), 8.54 (1H, d, J=8.7 Hz)

FAB-MASS (m/z): 454 ((M+1)$^+$), 307, 289

6) 5-[2-[2-[2-(7-Chloroquinolyl)]benzofuran-5-yloxy]-methyl]benzyl-1H-tetrazole mp: 153°–156° C.

IR (Nujol): 1620, 1600 cm$^{-1}$

NMR (DMSO-d$_6$, δ): 4.41 (2H, s), 5.30 (2H, s), 6.96 (1H, dd, J=2.2, 8.7 Hz), 7.27–7.44 (4H, m), 7.55–7.69 (3H, m), 7.80 (1H, s), 8.05 (1H, s, J=8.7 Hz), 8.10 (1H, s), 8.12 (1H, d, J=8.7 Hz), 8.52 (1H, d, J=8.7 Hz)

MASS (m/z): 467 (M$^+$), 424, 295

EXAMPLE 9

To a cooled suspension of 7-chloro-2-(5-hydroxybenzofuran-2-yl)quinoline (0.71 g) in N,N-dimethylformamide (10 ml), sodium hydride (60% in mineral oil, 0.11 g) was added below 10° C. After being stirred for 30 minutes, 3-bromomethylbenzonitrile (0.52 g) was added to the mixture. After being stirred at ambient temperature for 3 hours7 the resulting mixture was poured into ice-water (100 ml). The resulting precipitates were collected by filtration and washed with water, and dried in vacuo to give 3-[2-[2-(7-chloroquinolyl)]benzofuran-5-yloxy] methylbenzonitrile (1.0 g).

mp: 165°–167° C.

IR (Nujol): 2250, 1600, 1585 cm$^{-1}$

NMR (DMSO-d$_6$, δ): 5.24 (2H, s), 7.14 (1H, dd, J=2.6, 9.0 Hz), 7.39 (1H, d, J=2.6 Hz), 7.6–7.7 (3H, m), 7.8–7.87 (3H, m), 7.97 (1H, s), 8.07 (1H, d, J=8.7 Hz), 8.13 (1H, d, J=2.5 Hz), 8.16 (1H, d, J=8.7 Hz), 8.54 (1H, d, J=8.7 Hz)

MASS (m/z): 410 (M$^+$), 294

EXAMPLE 10

The following compounds were obtained according to a similar manner to that of Example 9.

1) Methyl 2-[2-[2-(7-chloroquinolyl)]benzofuran-5-yloxy] methylbenzoate mp: 193°–194° C.

IR (Nujol): 1720, 1615, 1595, 1580 cm$^{-1}$

NMR (CF$_3$COOD, δ): 4.03 (3H, s), 4.58 (2H, s), 7.4–8.4 (12H, m), 8.88 (1H, d, J=9.0 Hz)

MASS (m/z): 443 (M$^+$), 411, 295, 149

2) 2-[2-[2-(7-Chloroquinolyl)]benzofuran-5-yloxy]-methylbenzonitrile mp: 172°–175° C.

IR (Nujol): 2250, 1600 cm$^{-1}$

IR (DMSO-d$_6$, δ): 5.32 (2H, s), 7.15 (1H, dd, J=2.2, 8.7 Hz), 7.45 (1H, d, J=2.4 Hz), 7.56–7.82 (6H, m), 7.94 (1H, d, J=7.5 Hz), 8.08 (1H, d, J=8.7 Hz), 8.14 (1H, d, J=2.2 Hz), 8.18 (1H, d, J=8.7 Hz), 8.55 (1H, d, J=S.7 Hz)

MASS (m/z): 295, 230

3) 4-[2-[2-(7-chloroquinolyl)]benzofuran5-yloxy]-methylbenzonitrile mp: 196°–197° C.

IR (Nujol): 2250, 1605, 1585 cm$^{-1}$

NMR (DMSO-d$_6$, δ): 5.29 (2H, s), 7.14 (1H, dd, J=2.5, 9.0 Hz), 7.37 (1H, d, J=2.6 Hz), 7.6–7.7 (4H; m), 7.78 (1H, s), 7.89 (2H, d, J=8.4 Hz), 8.07 (1H, d, J=8.7 Hz), 8.13 (1H, d, J=2.5 Hz), 8.15 (1H, d, J=8.7 Hz), 8.54 (1H, d, J=8.7 Hz)

MASS (m/z): 410 (M$^+$), 294, 266

4) Methyl 3-[2-[2-(7-chloroquinolyl)]benzofuran-5-yloxy] methylbenzoate mp: 145°–147° C.

IR (Nujol): 1735, 1605 cm$^{-1}$

NMR (DMSO-d$_6$, δ): 3.88 (3H, s), 5.27 (2H, s), 7.14 (1H, dd, J=2.5, 9 Hz), 7.39 (1H, d, J=2.5 Hz), 7.54–7.8 (4H, m), 7.79 (1H, s), 7.94 (1H, d, J=7.6 Hz), 8.04–8.18 (4H, m), 8.53 (1H, d, J=8.7 Hz)

MASS (m/z): 443, 295 (base), 266, 238

EXAMPLE 11

A suspension of methyl 2-[2-[2-(7-chloroquinolyl)]-benzofuran-5-yloxy]methylbenzoate (2.0 g), 3N aqueous sodium hydroxide (4.5 ml) in a mixture of tetrahydrofuran (100 ml) and methanol (30 ml) was stirred at 60° C. for 2 hours. After the reaction mixture was filtered, the filtrate was concentrated under reduced pressure. To the resulting residue, water (100 ml) was added and the resulting suspension was adjusted to pH4 with diluted aqueous hydrochloric acid. After being stirred at ambient temperature for several minutes, the resulting precipitates were collected by filtration, washed with water and dried in vacuo to give 2-[2-[2-(7-chloroquinolyl)]benzofuran-5-yloxy] methylbenzoic acid (1.72 g).

mp: 234°–235° C.

IR (Nujol): 1710, 1600, 1580 cm$^{-1}$

NMR (DMSO-d$_6$, δ): 5.59 (2H, s), 7.12 (1H, m), 7.2–7.5 (3H, m), 7.65 (3H, m), 7.76 (1H, s), 7.89 (1H, d, J=7.0 Hz), 8.10 (3H, m), 8.52 (1H, d, J=8.7 Hz)

MASS (m/z): 429 (M⁺), 369, 295

EXAMPLE 12

A solution of 2-[2-[2-(7-chloroquinolyl)]benzofuran-5-yloxy]methylbenzoic acid (0.2 g), 5-amino-1H-tetrazole (48 ml), 4-dimethylaminopyridine (0.114 g) and 3-ethyl-1-[3-(dimethylaminopropyl]carbodiimide hydrochloride (0.178 g) in N,N-dimethylformamide (10 ml) was stirred at ambient temperature for 1 day, and then at 60° C. for 3 hours. After being cooled, the resulting solution was poured into ice-water. The resulting precipitates were collected by filtration and washed with water. The crude compound was subjected to column chromatography on silica gel and eluted with chloroform, successively with a mixture of chloroform and methanol (10:1). The fractions containing object compound were combined and concentrated under reduced pressure to give N-(1H-5-tetrazolyl)-2-[2-[2-(7-chloroquinolyl)]-benzofuran-5-yloxy]methylbenzamide (0.11 g).

mp: 222°–225° C.

IR (Nujol): 2700, 1650, 1600, 1570 cm⁻¹

NMR (DMSO-d₆, δ): 5.41 (2H, s), 7.08 (1H, d, J=9.2 Hz), 7.3–7.71 (8H, m), 8.06 (1H, d, J=8.8 Hz), 8.11 (1H, m), 8.13 (1H, d, J=7.0 Hz), 8.53 (1H, d, J=B.7 Hz)

FAB-MASS (m/z): 497 ((M+1)⁺), 307, 289

EXAMPLE 13

The following compounds were obtained according to a similar manner to that of Example 12.

1) N-[2-[2-[2-(7-Chloroquinolyl)]benzofuran-5-yloxy]-methoylbenzoyl]-2-methylbenzenesulfonamide mp: 277°–278° C.

IR (Nujol): 1700, 1600, 1580 cm⁻¹

NMR (DMSO-d₆, δ): 2.62 (3H, s), 5.27 (2H, s), 6.96 (1H, dd, J=2.6, 9.0 Hz), 7.16 (1H, d, J=2.3 Hz), 7.2–7.5 (5H, m), 7.57–7.72 (4H, m), 7.78 (1H, s), 7.98 (1H, d, J=6.4 Hz), 8.03 (1H, d, J=10.2 Hz), 8.09 (1H, m), 8.15 (1H, d, J=8.7 Hz), 8.54 ( 1H, d, J=8.7 Hz)

MASS (m/z): 582 (M⁺), 558, 470, 295

2) N-[3-[2-[2-(7-Chloroquinolyl)]benzofuran-5-yloxy]-methylbenzoyl]-2-methylbenzenesulfonamide mp: 144°–150° C. (dec.)

IR (Nujol): 3400, 1690, 1640, 1615, 1565 cm⁻¹

NMR (DMSO-d₆, δ): 2.63 (3H, s), 5.23 (2H, s), 7.13 (1H, dd, J=2.5, 9.0 Hz), 7.39 (1H, d, J=2.5 Hz), 7.4–7.9 (8H, m), 7.78 (1H, s), 8.0–8.2 (5H, m), 8.57 (1H, d, J=8.7 Hz), 12.8 (1H, br s)

FAB-MASS (m/z): 583 (M+1), 585, 308

3) N-[2-[2-(7-Chloroquinolyl)]-3-methylbenzofuran-5-ylcarbonyl]-2-methylbenzenesulfonamide mp: >300° C.

IR (Nujol): 3350, 1705, 1600, 1335, 1165 cm⁻¹

NMR (DMSO-d₆, δ): 2.63 (3H, s), 2.85 (3H, s), 7.3–7.5 (3H, m), 7.64 (1H, dd, J=2.2, 8.7 Hz), 7.68 (1H, d, J=8.7 Hz), 7.98 (1H, dd, J=2.2, 8.7 Hz), 8.0–8.15 (4H, m), 8.42 (1H, d, J=2.2 Hz), 8.55 (1H, d, J=8.7 Hz)

MASS (m/z): 490 (M⁺), 438, 412, 320

4) N-[2-(2-Quinolyl)benzofuran-5-ylcarbonyl]-2-methylbenzenesulfonamide

IR (Nujol): 3500, 1660, 1610, 1600, 1550, 1500, 1360, 1330, 1160 cm⁻¹

NMR (DMSO-d₆, δ): 2.59 (3H, s), 7.15–7.30 (3H, m), 7.59–7.66 (2H, m), 7.8–8.08 (6H, m), 8.15 (1H, d, J=9.0 Hz), 8.36 (1H, d, J=1.2 Hz), 8.52 (1H, d, J=8.7 Hz)

FAB-MASS (m/z): 481 (M+K)

5) N-[2-[2-(7-Chloroquinolyl)]benzofuran-5-ylcarbonyl]-2-methylbenzenesulfonamide mp: >300° C.

IR (Nujol): 3400, 1660 cm⁻¹

NMR (DMSO-d₆, δ): 2.59 (3H, s), 7.2–7.4 (3H, m), 7.6–7.7 (2H, m), 7.92 (1H, s), 7.95–8.0 (1H, m), 8.0–8.3 (4H, m), 8.37 (1H, s), 8.55 (1H, d, J=8.8 Hz)

FAB-MASS (m/z): 475 (M−1), 459, 305 ,

6) N-(1H-5-Tetrazolyl)-3-[2-[2-(7-chloroquinolyl)]-benzofuran-5-yloxy]methylbenzamide mp: 265° C. (dec.)

IR (Nujol) : 1660, 3600, 1570 cm⁻¹

NMR (DMSO-d₆, δ): 5.24 (23, s), 7.14 (1H, dd, J=2.6, 9.6 Hz), 7.39 (1H, d, J=2.6 Hz), 7.51–7.72 (4H, m), 7.79 (1H, s), 8.0–8.17 (5H, m), 8.53 (1H, d, J=8.7 Hz), 10.95 (1H, br s)

FAB-MASS (m/z): 497 (M+1), 460, 307

EXAMPLE 14

The following compounds Were obtained according to a similar manner to that of Example 3.

1) Chloro-2-(5-formylbenzofuran-2-yl)quinoline mp: 235°–236° C.

IR (Nujol): 1690, 1600 cm⁻¹

NMR (DMSO-d₆, δ): 7.75 (1H, dd, J=2.2, 8.7 Hz), 7.9–8.3 (6H, m), 8.4 (1H, d, J=2.2 Hz), 8.62 (1H, d, J=8.7 Hz), 10.14 (1H, s)

2) 7-Chloro-2-(7-formylbenzofuran-2-yl)quinoline

IR (Nujol): 1695, 1615 cm⁻¹

NMR (CDCl₃, δ): 7.45 (1H, t, J=7.6 Hz), 7.52 dd, J=8.7, 2.0 Hz), 7.75 (3H, S), 7.89 (1H, dd, J=7.6, 1.2 Hz), 7.97 (1H, dd, J=7.6, 1.2 Hz), 8.16 (1H, d, J=2.0 Hz), 8.16 (1H, d, J=8.6 Hz), 8.28 (1H, d, J=8.6 Hz), 10.62 (1H, s)

MASS (m/z): 307 (M⁺)

3) 7-Chloro-2-[6-(3-ethoxycarbonylpropoxy)benzofuran-2-yl]quinoline

IR (Nujol): 1740, 1735, 1625 cm⁻¹

NMR (CDCl₃, δ): 1.27 (3H, t, J=7.1 Hz), 2.17 (2H, tt, J=7.2, 6.1 Hz), 2.56 (2H, t, J=7.2 Hz), 4.09 (2H, t, J=6.1 Hz), 4.17 (2H, q, J=7.1 Hz), 6.91 (1H, dd, J=8.6, 2.2 Hz), 7.13 (1H, d, J=2.2 Hz), 7.46 (1H, dd, J=8.7, 2.0 Hz), 7.54 (1H, d, J=8.6 Hz), 7.54 (1H, s), 7.73 (1H, d, J=8.7 Hz), 7.94 (1H, d, J=S.7 Hz), 8.16 (1H, d, J=2.0 Hz), 8.18 (1H, d, J=8.7 Hz)

MASS (m/z): 409 (M⁺)

4) 7-Chloro-2-[6-(2-methoxycarbonyl-2-methylpropoxy)-benzofuran-2-yl]quinoline mp: 167°–168° C.

IR (Nujol): 1730, 1620, 1600 cm⁻¹

NMR (CDCl₃, δ): 1.36 (6H, s), 3.72 (3H, s), 4.04 (2H, s), 6.92 (1H, dd, J=8.6, 2.2 Hz), 7.13 (1H, d, J=2.2 Hz), 7.47 (1H, dd, J=8.7, 2.2 Hz), 7.54 (1H, d, J=8.6 Hz), 7.55 (1H, s), 7.74 (1H, d, J=S.7 Hz), 7.95 (1H, d, J=8.5 Hz), 8.16 (1H, d, J=2.1 Hz), 8.18 (1H, d, J=S.5 Hz)

MASS (m/z): 409 (M⁺)

5) 7-Chloro-2-(5-nitrobenzofuran-2-yl)quinoline

IR (Nujol): 1525, 1345 cm⁻¹

NMR (DMSO-d₆, δ): 7.65 (1H, dd, J=2.2, 8.7 Hz), 8.0–8.4 (6H, m), 8.62 (1H, d, J=8.7 Hz), 8.76 (1H, d, J=2.2 Hz)

MASS (m/z): 324 (M⁺), 294, 278, 249, 215

EXAMPLE 15

The following compound was obtained according to similar manners to those of Preparation 1 and Example 1.

7-Hydroxy-2-[5-(3-ethoxycarbonylpropoxy)benzofuran-2-yl]quinoline mp: 121°–122° C.

IR (Nujol): 1740, 1610, 1600 cm$^{-1}$

NMR (CDCl$_3$, δ): 1.27 (3H, t, J=7.1 Hz),2.16 (2H, tt, J=7.3, 6.1 Hz), 2.56 (2H, t, J=7.3 Hz), 4.07 (2H, t, J=6.1 Hz), 4.17 (2H, q, J=7.1 Hz), 6.98 (1H, dd, J=8.9, 2.5 Hz), 7.11 (1H, d, J=2.5 Hz), 7.45 (1H, dd, J=8.7, 2.0 Hz), 7.51 (1H, d, J=8.9 Hz), 7.57 (1H, s), 7.75 (1H, d, J=8.7 Hz), 7.99 (1H, d, J=8.7 Hz), 8.18 (1H, d, J=2.0 Hz), 8.20 (1H, d, J=8.7 Hz)

MASS (m/z): 409 (M$^+$), 364

EXAMPLE 16

The following compounds were obtained according to a similar manner he that of Example 11.

1) 3-[2-[2-(7-Chloroquinolyl)]benzofuran-5-yloxy] methylbenzoic acid

IR (Nujol): 1690, 1600, 1590 cm$^{-1}$

NMR (DMSO-d$_6$, δ): 5.24 (2H, s), 7.13 (1H, dd, J=2.5, 9.0 Hz), 7.38 (1H, d, J=2.5 Hz), 7.51 (1H, d, J=7.6 Hz), 7.6–7.8 (3H, m), 7.79 (1H, s), 7.92 (1H, d, J=7.6 Hz), 8.0–8.2 (4H, m), 8.53 (1H, d, J=8.7 Hz)

2) 7-Chloro-2-(5-carboxy-3-methylbenzofuran-2-yl)-quinoline

IR (Nujol): 3335, 1680, 1620 cm$^{-1}$

NMR (CF$_3$COOH, δ): 2.90 (3H, s), 7.7–8.8 (7H, m), 8.95 (1H, d, J=9.2 Hz)

MASS (m/z): 337 (M$^+$, base) 308

3) 2-[2-(7-Chloroquinolyl)]-3-methoxybenzofuran-5-ylcarboxylic acid

IR (Nujol): 2500, 1700, 1640, 1600 cm$^{-1}$

NMR (DMSO-d$_6$, δ): 7.64 (1H, dd, J=2.2, 8.7 Hz), 7.81 (1H, d, J=8.7 Hz), 8.05 (2H, d, J=8.7 Hz), 8.15 (1H, d, J=2.2 Hz), 8.20 (1H, d, J=8.7 Hz), 8.49 (1H, d, J=2.2 Hz), 8.53 (1H, d, J=8.7 Hz)

MASS (m/z): 353 (M$^+$), 324, 308

4) 2-(2-Quinolyl)benzofuran-5-ylcarboxylic acid

IR (Nujol): 3300, 2600, 1680 cm$^{-1}$

NMR (DMSO-d$_6$, δ): 7.67 (1H, t, J=7.0 Hz) 7.8–8.0 (2H, m), 8.0–8.1 (3H, m), 8.16 (1H, d, J=8.7 Hz), 8.20 (1H, dd, J=8.6, 1.5 Hz), 8.42 (1H, d, J=1.5 Hz), 8.58 (1H, d, J=8.7 Hz)

MASS (m/z): 289 (M$^+$, base)

5) 2-[2-(7-Chloroquinolyl)]benzofuran-5-ylcarboxylic acid

IR (Nujol): 2700, 1680 cm$^{-1}$

NMR (DMSO-d$_6$, δ): 7.69 (1H, dd, J=2.2, 8.6 Hz), 7.83 (1H, d, J=8.6 Hz), 7.98 (1H, s), 8.04 (1H, dd, J=2.0, 8.6 Hz), 8.10 (1H, d, J=8.8 Hz), 8.16 (1H, d, J=2.2 Hz), 8.21 (1H, d, J=8.6 Hz), 8.41 (1H, d, J=2.0 Hz), 8.59 (1H, d, J=8.8 Hz)

MASS (m/z): 323 (M$^+$), 307

EXAMPLE 17

To a solution of N-[2-(2-quinolyl)benzofuran-5-ylcarbonyl]-2-methylbenzenesulfonamide (0.25 g) in ethyl acetate (100 ml) was added saturated hydrogen chloride in ethyl acetate. The resulting precipitates were collected by filtration and washed with ethyl acetate and ethanol to give N-[2-(2-quinolyl)benzofuran-5-ylcarbonyl]-2-methylbenzenesulfonamide hydrochloride (0.19 g).

mp: 210°–215° C.

IR (Nujol): 2600, 1690, 1640, 1620, 1600, 1345, 1160 cm$^{-1}$

NMR (DMSO-d$_6$, δ): 2.66 (3H, s), 7.4–7.7 (4H, m), 7.8–8.2 (8H, m), 8.43 (1H, s), 8.58 (1H, d, J=8.6HZ), 6.4 (2H)

EXAMPLE 18

The following compound was obtained according to similar manners to those of Examples 12 and 17.

N-[2-[2-(7-Chloroquinolyl)]-3-methoxybenzofuran-5-ylcarbonyl]-2-methylbenzenesulfonamide hydrochloride mp: 208°–210° C. (dec.)

IR (Nujol): 2600, 1700, 1630, 1615, 1600, 1575, 1350, 1170 cm$^{-1}$

NMR (DMSO-d$_6$, δ): 2.67 (3H, s), 4.37 (3H, s), 4.89 (1H, br), 7.4–7.6 (3H, m), 7.65 (1H, dd, J=2.2, 8.6 Hz), 7.83 (1H, d, J=8.7 Hz), 7.95 (1H, dd, J=2.2, 8.6 Hz), 8.08 (1H, d, J=8.7 Hz), 8.11 (1H, dd, J=2.2, 8.6 Hz), 8.14 (1H, d, J=2.2 Hz), 8.22 (1H, d, J=8.6 Hz), 8.55 (1H, d, J=8.7 Hz), 8.64 (1H, d, J=2.2 Hz), 12.8 (1H, br s)

MASS (m/z): 506, 380, 365, 351

EXAMPLE 19

A mixture of 7-chloro-2-(2,4-diformylphenoxymethyl)-quinoline (5.7 g) and pyridine hydrochloride (11.4 g) in toluene (140 ml) was stirred under reflux for 2 hours. After being cooled, the appeared crystals were collected, washed with toluene and water. The resulting crystals were washed with ethanol (100 ml) and dried to give 7-chloro-2-(5-formylbenzofuran-2-yl)quinoline (4.67 g).

mp: 235°–236° C.

IR (Nujol): 1690, 1600 cm$^{-1}$

NMR (DMSO-d$_6$, δ): 7.72 (1H, dd, J=2.2, 8.7 Hz), 7.9–8.3 (6H, m), 8.4 (1H, d, J=2.2 Hz), 8.62 (1H, d, J=8.7 Hz), 10.14 (1H, s)

MASS (m/z): 307 (M$^+$, base) 278

EXAMPLE 20

The following compound was obtained according to a similar manner to that of Example 19.

7-Chloro-2-(5-methoxycarbonyl-3-methylbenzofuran-2-yl)quinoline

IR (Nujol): 1730, 1715, 1615, 1600 cm$^{-1}$

NMR (CF$_3$COOH, δ): 2.90 (3H, s), 4.10 (3H, s), 7.6–8.5 (6H, m), 8.55 (1H, s), 9.05 (1H, d, J=9.0 Hz)

MASS (m/z) : 351 (M$^+$, base)

EXAMPLE 21

To a being cooled suspension of 7-chloro-2-[2,4-bis-(methoxycarbonyl)phenoxymethyl]quinoline (0.3 g) in N,N-dimethylformamide (6 ml), sodium hydride ((60% in mineral oil) 31 mg). After being stirred at same temperature for 30 minutes and successively at ambient temperature for 3 hours, the resulting mixture was poured into a mixture of ethyl acetate and buffer (pH 4.1). The appeared precipitates were collected by filtration and washed with n-hexane to give 7-chloro-2-(5-methoxycarbonyl-3-hydroxybenzofuran-2-yl)quinoline (0.15

IR (Nujol) : 1720, 1630, 1600 cm$^{-1}$

NMR (DMSO-d$_6$, δ): 3.90 (3H, s), 7.6 (1H, dd, J=2.2, 8.7 Hz), 7.75 (1H, d, J=8.7 Hz), 7.9–8.2 (4H, m), 8.48 (1H, d, J=8.7 Hz), 8.50–8.55 (1H, m)

MASS (m/z) : 353 (M$^+$, base) 324, 294, 266

EXAMPLE 22

A mixture of 2-(2,4-diformylphenoxymethyl)quinoline (164.6 mg) and sodium methoxide (140 mg) in methanol (10.5 ml) was stirred under reflux for 30 minutes. The reaction mixture was concentrated under reduced pressure, and to the residue was added water and chloroform. The separated organic layer was washed with brine, dried over magnesium sulfate and concentrated under reduced pressure to give a crude residue. The residue was subjected to column chromatography on silica gel and eluted with a mixture of ethyl acetate and n-hexane (1:10). The fractions containing object compound were combined and concentrated under reduced pressure to give 2-(5-formylbenzofuran-2-yl) quinoline (31 mg).

NMR (CDCl$_3$, δ): 7.58 (1H, ddd, J=8.1, 6.9, 1.2 Hz), 7.72 (1H, s), 7.76 (1H, d, J=8.5 Hz), 7.78 (1H, ddd, J=8.3, 6.9, 1.5 Hz), 7.86 (1H, dd, J=8.1, 1.5 Hz), 7.95 (1H, dd, J=8.5, 1.7 Hz), 8.05 (1H, d, J=8.6 Hz), 8.21 (1H, dd, J=8.3, 1.2 Hz), 8.24 (1H, d, J=1.7 Hz), 8.29 (1H, d, J=8.6 Hz), 10.11 (1H, s)

EXAMPLE 23

A mixture of 7-chloro-2-[6-[3-(ethoxycarbonyl)-propoxy] benzofuran-2-yl]quinoline (1.26 g) and potassium hydroxide (1.51 g) in a mixture of ethanol (12 ml) and water (6 ml) was stirred under reflux for one hour. After being cooled, the resulting precipitates were collected by filtration, washed with ethanol and added to water. The mixture was adjusted to pH 7 with diluted aqueous hydrochloric acid. The resulting crystals were collected by filtration, washed with water, and recrystallized from a mixture of acetic acid and methanol to give 7-chloro-2-[6-(3-carboxypropoxy)benzofuran-2-yl]quinoline (0.65 g).

mp: 200°–201° C.

IR (Nujol): 1710, 1630 cm$^{-1}$

NMR (DMSO-d$_6$, δ): 2.00 (2H, t, J=7.3 Hz), 2.44 tt, J=7.3, 6.4 Hz), 4.10 (2H, t, J=6.4 Hz), 6.97 (1H, dd, J=8.6, 2.2 Hz), 7.34 (1H, d, J=2.2 Hz), 7.63 (1H, dd, J=8.7, 2.1 Hz), 7.65 (1H, d, J=8.6 Hz), 7.79 (1H, s), 8.05 (1H, d, J=8.7 Hz), 8.10 (1H, d, J=2.1 Hz), 8.11 (1H, d, J=8.6 Hz), 8.51 (1H, d, J=8.6 Hz)

MASS (m/z): 381 (M$^+$)

EXAMPLE 24

The following compounds were obtained according to a similar manner to that of Example 23.

1) Chloro-2-[6-(2-carboxy-2-methylpropoxy)benzofuran-2-yl]quinoline mp: 246°–249° C.

IR (Nujol): 1720, 1620, 1600 cm$^{-1}$

NMR (DMSO-d$_6$, δ): 1.26 (6H, s), 4.06 (2H, s), 6.96 (1H, dd, J=8.6, 2.2 Hz), 7.34 (1H, d, J=2.2 Hz), 7.64 (1H, dd, J=8.7, 2.1 Hz), 7.65 (1H, d, J=8.6 Hz), 7.80 (1H, S), 8.06 (1H, a, J=8.7 Hz), 8.11 (1H, d, J=2.1 Hz), 8.12 (1H, d, J=8.5 Hz), 8.52 (1H, d, J=8.5 Hz)

MASS (m/z): 395 (M$^+$)

2) 7-Chloro-2-[5-(2-carboxy-2-methylpropyl)benzofuran-2-yl]quinoline mp: 198°–199° C.

IR (Nujol): 1710, 1600 cm$^{-1}$

NMR (DMSO-d$_6$, δ): 1.12 (6H, s), 2.92 (2H, s), 7.24 (1H, dd, J=8.5, 1.8 Hz), 7.54 (1H, d, J=1.8 Hz), 7.65 (1H, d, J=8.5 Hz), 7.67 (1H, dd, J=8.7, 2.1 Hz), 7.83 (1H, s), 8.08 (1H, d, J=8.7 Hz), 8.14 (1H,, d, J=2.1 Hz), 8.18 (1H, d, J=8.5 Hz), 8,55 (1H, d, J=8.5 Hz)

MASS (m/z): 379 (M$^+$)

3) 7-Chloro-2-[5-(3-carboxypropoxy)benzofuran-2-yl]-quinoline mp: 229°–233° C.

IR (Nujol): 1715, 1600 cm$^{-1}$

NMR (DMSO-d$_6$, δ): 2.00 (2H, t, J=7 Hz), 2.39 (2H, t, J=7 Hz), 4.02 (2H, t, J=7 Hz), 7.05 (1H, dd, J=9, 2 Hz), 7.27 (1H, d, J=2 Hz), 7.66 (1H, d, J=9 Hz), 7.69 (1H, dd, J=9, 2 Hz), 7.78 (1H, s), 8.10 (1H, d, J=9 Hz), 8.17 (1H, d, J=2 Hz), 8.19 (1H, d, J=9 Hz), 8.58 (1H, d/J=9 Hz)

MASS (m/z): 381 (M$^+$), 295

4) 7-Chloro-2-[5-(2-carboxy-1-hydroxy-2-methylpropyl)-benzofuran-2-yl]quinoline mp: 199°–202° C. (dec.)

IR (Nujol): 3400, 1700, 1600 cm$^{-1}$

NMR (DMSO-d$_6$, δ): 0.96 (3H, s), 0.99 (3H, s), 4.77 (1H, s), 7.39 (1H, br d, J=8.8 Hz), 7.6–7.7 (3H, m), 7.85 (1H, s), 8.07 (1H, d, J=8.8 Hz), 8.14 (1H, br s), 8.17 (1H, d, J=8.7 Hz), 8.54 (1H, d, J=8.7 Hz)

MASS (m/z): 395 (M$^+$)

EXAMPLE 25

A mixture of 7-chloro-2-[5-(2-carboxy-2-methylpropyl) benzofuran-2-yl]quinoline (75.8 mg) and 1,1'-carbonyldiimidazole (115 mg) in N,N-dimethylformamide (1 ml) was stirred for 4 days at ambient temperature. To the resulting mixture 5-amino-1H-tetrazole monohydrate (100 mg) was added. The reaction mixture was stirred for 3 weeks at ambient temperature and poured into ice-water.

The resulting precipitates were collected by filtration and washed with water. The crude compound was subjected to column chromatography on silica gel and eluted with a mixture of chloroform and methanol (10:1). The fractions containing object compound were combined and concentrated under reduced pressure to give 7-chloro-2-[5-[2-methyl-2-(1H-tetrazol-5-yl)carbamoylpropyl]benzofuran-2-yl]-quinoline (43 mg).

IR (Nujol): 1660, 1600cm$^{-1}$

NMR (DMSO-d$_6$, δ): 1.24 (6H, s), 3.09 (2H, s), 7.05 (2H, br s), 7.29 (1H, d, J=9 Hz), 7.56 (1H, s), 7.65 (1H, d, J=9 Hz), 7.66 (1H, d, J=9 Hz), 7.80 (1H, s), 8.07 (1H, d, J=9 Hz), 8.15 (1H, s), 8.21 (1H, d, J=9 Hz), 8.54 (1H, d, J=9 Hz)

MASS (m/z): 446 (M$^+$)

EXAMPLE 26

To a cooled solution of 7-chloro-2-(5-formylbenzofuran-2-yl)quinoline (0.92 g) in a mixture of methanol (20 ml) and chloroform (10 ml) was added sodium borohydride (0.40 g) in small portions. After being stirred at the same temperature for 2 hours, the resulting mixture was treated with diluted hydrochloric acid and adjusted to be basic with aqueous sodium hydrogen carbonate. The resulting precipitates were collected by filtration, Washed with water and dried to give 7-chloro-2-(5-hydroxymethylbenzofuran-2-yl)quinoline (0.81 g).

NMR (CDCl$_3$, δ): 2.59 (1H, br s), 4.78 (2H, s), 7.42 (1H, dd, J=8.5, 1.7 Hz), 7.52 (1H, dd, J=8.7, 2.0 Hz), 7.60 (1H, d, J=8.5 Hz), 7.73 (1H, s), 7.77 (1H, d, J=1.7 Hz), 7.80 (1H, d, J=8.7 Hz), 8.06 (1H, d, J=8.7 Hz), 8.26 (1H, d, J=2.0 Hz), 8.28 (1H, d, J=8.7 Hz)

MASS (m/z): 309 (M$^+$)

EXAMPLE 27

To a mixture of 7-chloro-2-(2-methoxycarbonylbenzofuran-5-yl)quinoline (0.92 g) in tetrahydrofuran (10 ml), lithium aluminum hydride (76.7 mg) was added dropwise under ice cooling. After being stirred for 2 hours, the resulting mixture was poured into a mixture of ice and diluted aqueous hydrochloric acid and extracted with ethyl acetate. The organic layer was washed with brine, dried over magnesium sulfate, and concentrated under reduced pressure. The residue was subjected to column chromatography on silica gel and eluted with a mixture of ethyl acetate and toluene. The fractions containing object compound were combined, concentrated under reduced pressure, and recrystallized from toluene to give 7-chloro-2-(2-hydroxymethylbenzofuran-5-yl)quinoline (0.58 mp: 206°–207° C.

IR (Nujol): 3300, 1610 cm$^{-1}$

NMR (CDCl$_3$, δ): 4.81 (2H, s), 6.77 (1H, s), 7.48 (1H, dd, J=8.7, 2.1 Hz), 7.59 (1H, d, J=8.7 Hz), 7.77 (1H, d, J=8.7 Hz), 7.92 (1H, d, J=B.7 Hz), 8.11 (1H, dd, J=8.7, 1.8 Hz), 8.21 (1H, d, J=8.7 Hz), 8.21 (1H, d, J=2.0 Hz), 8.35 (1H, d, J=1.8 Hz)

MASS (m/z): 309 (M$^+$), 292, 282

EXAMPLE 28

A mixture of 7-chloro-2-(5-hydroxymethylbenzofuran-2-yl)quinoline (0.40 g) and thionyl chloride (0.30 g) in chloroform (20 ml) was stirred under reflux for 1 hour. After being cooled, the resulting mixture was adjusted to pH 7 with aqueous sodium hydrogen carbonate. The organic layer was washed with brine, dried over magnesium sulfate and concentrated under reduced pressure to give 7-chloro-2-(5-chloromethylbenzofuran-2-yl)quinoline (0.47 g).

NMR (CDCl$_3$, δ): 4.74 (2H, s), 7.42 (1H, dd, J=8.6, 1.8 Hz), 7.50 (1H, dd, J=8.7 Hz), 7.61 (1H, s), 7.62 (1H, d, J=8.6 Hz), 7.71 (1H, d, J=1.8 Hz), 7.77 (1H, d, J=8.7 Hz), 8.02 (1H, d, J=8.6 Hz), 8.19 (1H, d, J=2.0 Hz), 8.23 (1H, d, J=8.6 Hz)

MASS (m/z): 327 (M$^+$)

EXAMPLE 29

A mixture of 7-chloro-2-(5-Chloromethylbenzofuran-2-yl)quinoline (0.45 g), methyl 2-mercaptopropionate (0.27 g), potassium carbonate (1.7 g) and Aliquat 336 (phase transfer 0.1 g) in a mixture of toluene (60 ml) and water (5 ml) was stirred at ambient temperature for 2 days. The organic layer was separated, washed with brine, dried over magnesium sulfate and concentrated in reduced pressure. The resulting residue was subjected to column chromatography on silica gel and eluted with a mixture of ethyl acetate and toluene (1:10). The fractions containing object Compound were combined and concentrated under reduced pressure to give 7-chloro-2-[5-[2-(methoxycarbonyl)ethylthiomethyl]benzofuran-2-yl]quinoline (0.38 g).

mp: 96°–103° C.

IR (Nujol): 1745, 1730, 1600 cm$^{-1}$

NMR (CDCl$_3$, δ): 2.54–2.62 (2H, m), 2.64–2.78 (2H, m), 3.69 (3H, s), 3.87 (2H, s), 7.36 (1H, dd, J=8.6, 1.8 Hz), 7.50 (1H, dd, J=8.7, 2.1 Hz), 7.58 (1H, d, J=8.6 Hz), 7.59 (1H, s), 7.63 (1H, d, J=8.5 Hz), 7.76 (1H, d, J=8.9 Hz), 8.01 (1H, d, J=8.5 Hz), 8.20 (1H, d, J=2.1 Hz), 8.22 (1H, d, J=8.5 Hz)

MASS (m/z): 411 (M$^+$)

EXAMPLE 30

The following compound was obtained according to a similar manner to that of Example 29.

7-Chloro-2-[5-[2-(dimethylcarbamoyl)ethylthiomethyl]-benzofuran-2-yl]quinoline mp: 139°–140° C.

IR (Nujol): 1645, 1620, 1605 cm$^{-1}$

NMR (CDCl$_3$, δ): 2.53 (2H, t, J=7.6 Hz), 2.81 (2H, t, J=7.6 Hz), 2.92 (3H, s), 2.93 (3H, s), 3.88 (2H, s), 7.39 (1H, dd, J=8.3, 1.8 Hz), 7.49 (1H, dd, J=8.6, 2.1 Hz), 7.56 (1H, d, J=8.3 Hz), 7.58 (1H, s), 7.63.(1H, d, J=1.8 Hz), 7.76 (1H, d, J=8.6 Hz), 8.01 (1H, d, J=8.5 Hz), 8.19 (1H, d, J=2.1 Hz), 8.22 (1H, d, J=8.5 Hz)

MASS (m/z): 424 (M$^+$)

EXAMPLE 31

A mixture of 7-chloro-2-(5-nitrobenzofuran-2-yl)-quinoline (1.7 g), 10% aqueous hydrochloride (20 ml) and tin(II) chloride bihydrate (4.0 g) in ethanol (10 ml) was stirred mechanically under reflux for 7 hours. After being cooled, the resulting mixture was made basic with aqueous sodium hydroxide and filtered. The precipitates were dissolved into tetrahydrofuran (100 ml) and filtered. The filtrate was concentrated under reduced pressure to give crude materials, which were purified by column chlomatography to give 7-chloro-2-(5-aminobenzofuran-2-yl)quinoline (0.73 g).

IR (Nujol): 3400, 3320, 1620, 1660, 1550 cm$^{-1}$

NMR (DMSO-d$_6$, δ): 6.74 (1H, dd, J=2.6, 8.7 Hz), 6.84. (1H, d, J=2.6 Hz), 7.40 (1H, d, J=8.7 Hz), 7.5–7.7 (3H, m), 8.0–8.2 (4H, m), 8.50 (1H, d, J=8.7 Hz)

MASS (m/z): 294 (M$^+$base) 265

EXAMPLE 52

A mixture of 7-Chloro-2-(5-aminobenzofuran-2-yl)-quinoline (0.17 g), sodium bicarbonate (0.2 g), ethyl 4-bromobutyrate (0.12 g) in hexamethylphosphoric triamide ml) was stirred at ambient temperature for 1 day. The resulting mixture was poured into ice-water. The appeared precipitates were collected by filtration, washed with water, and recrystallized from ethanol to give 7-chloro-2-[5-(3-ethoxycarbonylpropylamino)benzofuran-2-yl]quinoline (0.13 g).

mp: 154°–155° C.

IR (Nujol): 3400, 1730, 1600 cm$^{-1}$

NMR (CDCl$_3$, δ): 1.27 (3H, t, J=7.2 Hz), 2.47 (2H, t, J=7.2 Hz), 3.24 (2H, t, J=7.2 Hz), 4.15 (2H, q, J=7.2 Hz), 6.73 (1H, dd, J=2.2, 8.7 Hz), 6.84 (1H, d, J=2.2 Hz), 7.40–7.48 (3H, m), 7.72 (1H, d, J=8.8 Hz), 7.94. (1H, d, J=8.8 Hz), 8.15–8.20 (2H, m)

MASS (m/z): 408 (M$^+$), 362, 307, 294 (base)

EXAMPLE 33

To a mixture of 7-chloro-2-(5-aminobenzofuran-2-yl)-quinoline (0.28 g) and pyridine (0.12 ml) in a mixture of dichloromethane (10 ml) and N,N-dimethylformamide (20 ml), 2,2-dimethylsuccinic anhydride was added dropwise at ambient temperature. After being stirred at ambient temperature for 1 day, the resulting mixture was poured into ice-water. The appeared precipitates were collected by filtration, washed with water and recrystallized from ethanol to give 7-chloro-2-[5-(3-carboxy-3-methylbutyrylamino) benzofuran-2-yl]quinoline (0.13 g).

mp: 228°–230° C.

IR (Nujol): 3350, 1710, 1680, 1645, 1600 cm$^{-1}$

NMR (DMSO-d$_6$, δ): 1.24 (6H, s), 2.62 (2H, s), 7.45 (1H, dd, J=2.2, 8.7 Hz), 7.66 (1H, dd, J=2.3, 8.6 Hz), 7.84 (1H, s), 8.08 (1H, d, J=8.6 Hz), 8.1–8.2 (3H, m), 8.55 (1H, d, J=8.6 Hz), 10.03 (1H, s)

MASS (m/z): 404 (M$^+$), 320, 294 (base)

EXAMPLE 34

To a cooled suspension of lithium diisopropylamide {(1.45 mM tetrahydrofuran and n-hexane solution), 4 ml}, methyl 2-methylpropionate (592 mg) was added at –78° C. The reaction mixture was stirred at same temperature for 30 minutes. Subsequently trimethylchlorosilane (630 mg) was added to the mixture at –78° C. After being stirred for 1 hour at ambient temperature, the mixture was filtered and the filtrate was concentrated under reduced pressure. To the mixture of the residue and 7-chloro-2-(5-formylbenzofuran-2-yl)quinoline (0.79 g) in dichloromethane (10 ml), titanium (IV) tetrachloride (1.2 ml) was added at –78° C. The reaction mixture was stirred at same temperature for 30 minutes and at ambient temperature for 1 hour. The mixture was poured into ice cooled aqueous potassium carbonate solution. The mixture was filtered and the residue was washed with chloroform. The filtrate was concentrated under reduced pressure. The residue was subjected to column chromatography on silica gel and eluted with a mixture of ethyl acetate and chloroform (1:10). The fractions containing object compound were combined and concentrated under reduced pressure to give 7-chloro-2-[5-(1-hydroxy-2-methoxycarbonyl-2-methylpropyl)benzofuran-2-yl] quinoline (0.07 g).

mp: 162°–163° C.

IR (Nujol): 1730, 1600 cm$^{-1}$

NMR (CDCl$_3$, δ): 1.16 (3H, s), 1.20 (3H, s), 3.23 (1H, d, J=4.0 Hz), 3.75 (3H, s), 5.04 (1H, d, J=4.0 Hz), 7.33 (1H, dd, J=8.6, 1.8 Hz), 7.49 (1H, dd, J=8.7, 2.1 Hz), 7.58 (1H, d, J=8.6 Hz), 7.61 (1H, s), 7.64 (1H, d, J=1.8 Hz), 7.76 (1H, d, J=8.7 Hz), 8.01 (1H, d, J=8.6 Hz), 8.20 (1H, d, J=2.1 Hz), 8.22 (1H, d, J=8.6 Hz) 409 (M$^+$)

MASS (m/z): 409 (M$^+$)

EXAMPLE 35

To a cooled suspension of lithium diisopropylamide {(1.45 mM tetrahydrofuran and n-hexane solution), 3.1 ml} and methyl 2-methylpropionate (0.5 g), dried hexamethylphosphoric triamide (0.5 ml) was added at –78° C. and the mixture was stirred for 10 minutes at the same temperature. Subsequently, 7-chloro-2-(5-chloromethylbenzofuran-2-yl)quinoline (6.43 g) was added to the mixture. After being stirred for 30 minutes at the same temperature, additive hexamethylphosphoric triamide (1.36 ml) was added to the mixture. The reaction temperature was gradually elevated to –10° C. for 1 hour. The resulting mixture was poured into ice-water and extracted with chloroform. The organic layer was washed with brine, dried over sodium sulfate and concentrated under reduced pressure. The residue was subjected to column chromatography on silica gel (100 g) and eluted with n-hexane, successively 10% ethyl acetate in n-hexane and toluene. The fractions containing object compound were combined and concentrated under reduced pressure. The residue was dissolved in chloroform and n-hexane was added to the solution. The resulting precipitates were collected by filtration and dried to give 7-chloro-2-[5-(2-methoxycarbonyl-2-methylpropyl)benzofuran-2-yl]-quinoline (0.18 g).

mp: 137°–138° C.

IR (Nujol): 1735, 1620, 1600 cm$^{-1}$

NMR (CDCl$_3$, δ): 1.23 (6H, s), 2.97 (2H, s), 3.67 (3H, s), 7.12 (1H, dd, J=8.5, 1.8 Hz), 7.41 (1H, d, J=1.8 Hz), 7.49 (1H, dd, J=8.6, 2.1 Hz), 7.51 (1H, d, J=8.5 Hz), 7.57 (1H, s), 7.76 (1H, d, J=8.6 Hz), 8.01 (1H, d, J=8.5 Hz), 8.19 (1H, d, J=2.1 Hz), 8.21 l1H, d, J=8.5 Hz)

MASS (m/z): 393 (M$^+$), 362

EXAMPLE 36

A mixture of 5-acetyl-2-methoxycarbonylbenzofuran (0.57 g), 2-amino-4-chlorobenzaldehyde (0.40 g) and p-toluenesulfonic acid monohydrate (0.04 mg) was stirred at 200° C. for 3 hours. After being cooled, the resulting mixture was dissolved in chloroform, washed with water, dried over magnesium sulfate and concentrated under reduced pressure to give a syrup. The syrup was subjected to column chromatography on silica gel and eluted with a mixture of ethyl acetate and toluene (1:20). The fractions containing object compound were combined and concentrated under reduced pressure to give 7-chloro-2-(2-methoxycarbonylbenzofuran-5-yl)quinoline (0.32 g).

mp: 178°–181° C.

IR (Nujol): 1730, 1610 cm$^{-1}$

NMR (CDCl$_3$, δ): 4.01 (3H, s), 7.49 (1H, dd, J=8.7, 2.0 Hz), 7.64 (1H, s), 7.73 (1H, d, J=8.8 Hz), 7.78 (1H, d, J=8.7 Hz), 7.91 (1H, d, J=8.7 Hz), 8.18 (1H, d, J=2.0 Hz), 8.22 (1H, d, J=8.7 Hz), 8.29 (1H, dd, J=8.8, 1.8 Hz), 8.49 (1H, d, J=1.8 Hz)

MASS (m/z): 337 (M$^+$)

EXAMPLE 37

A mixture of 7-chloro-2-(2-hydroxymethylbenzofuran-5-yl)quinoline (767.9 mg) and manganese (IV) oxide (5.01 g) in chloroform (80 ml) was stirred for 5 hours at ambient temperature. The resulting mixture was filtered and the filtrate was concentrated in reduced pressure to give 7-chloro-2-(2-formylbenzofuran-5-yl)quinoline (650.9 g).

NMR (CDCl$_3$, δ): 7.51 (1H, ad, J=8.6, 2.0 Hz), 7.68 (1H, s), 7.75 (1H, d, J=8.8 Hz), 7.79 (1H, d, J=8.6 Hz), 7.92 (1H, d, J=8.7 Hz), 8.19 (1H, d, J=2.0 Hz), 8.25 (1H, d, J=8.7 Hz), 8.37 (1H, dd, J=8.8, 1.8 Hz), 8.56 (1H, a, J=1.8 Hz), 9.92 (1H,

MASS (m/z): 307 (M$^+$), 280

EXAMPLE 38

A mixture of 2-(5-formylbenzofuran-2-yl)quinoline (0.92 g), manganese (IV) oxide (4.6 g), sodium cyanide (2.2 g) and acetic acid (0.6 ml) in methanol (200 ml) was stirred at ambient temperature for 1.5 hours. The resulting mixture was filtered and filtrate was poured into water (400.ml). The appeared precipitates were collected by filtration and washed with water. The precipitates were subjected to column chromatography on silica gel and eluted with a mixture of toluene and ethyl acetate (50:1). The fractions containing objected compound were combined and concentrated under reduced pressure to give 2-(5-methoxycarbonylbenzofuran-2-yl)-quinoline (0.48 g).

IR (Nujol): 1726, 1600; 1550, 1500 cm$^{-1}$

NMR (CDCl$_3$, δ): 3.96 (3H, s), 7.65 (1H, s), 7.5–7.9 (4H, m), 8.02 (1H, d, J=8.6 Hz), 8.09 (1H, dd, J=2.6, 8.8 Hz), 8.19 (1H, d, J=8.6 Hz), 8.26 (1H, d, J=8.8 Hz), 8.42 (1H, d, J=0.6 Hz)

MASS (m/z): 303 (M$^+$, base), 272, 244, 215

EXAMPLE 39

The following compound was obtained according to a similar manner to that of Example 38.

7-Chloro-2-(5-methoxycarbonylbenzofuran-2-yl)-quinoline

IR (Nujol): 1720, 1615, 1600 cm$^{-1}$

NMR (DMSO-d$_6$, δ): 3.90 (3H, s), 7.78 (1H, dd, J=2.2, 8.6 Hz), 7.85 (1H, d, J=8.6 Hz), 7.96 (1H, s), 8.0–8.2 (5H, m), 8.43 (1H, d, J=1.2 Hz), 8.57 (1H, d, J=8.7 Hz)

MASS (m/z): 337 (M$^+$), 306

EXAMPLE 46

A mixture of 7-chloro-2-(5-methoxycarbonyl-3-hydroxybenzofuran-2-yl)quinoline (1.0 g), potassium carbonate (0.39 g), and methyl iodide (0.40 g) in a mixture of tetrahydrofuran (20 ml) and N,N-dimethylformamide (8 ml) was stirred under reflux. After being cooled, the appeared precipitates were collected by filtration and washed with acetone to give 7-chloro-2-(5-methoxycarbonyl-3-methoxybenzofuran-2-yl)quinoline (0.51 g).

IR (Nujol): 1730, 1620, 1600, 1580, 1560 cm$^{-1}$

NMR (DMSO-d$_6$, δ): 3.92 (3H, s), 4.32 (3H, s), 7.78 (1H, dd, J=2.2, 8.7 Hz), 7.87 (1H, d, J=8.7 Hz), 8.07 (2H, d, J=8.7 Hz), 8.17 (1H, d, J=2.2 Hz), 8.23 (1H, d, J=8.7 Hz), 8.51 (1H, d, J=2.2 Hz), 8.54 (1H, d, J=8.7 Hz)

MASS (m/z) : 367 (M$^+$, base) 352, 338, 162

EXAMPLE 41

To a cooled mixture of 7-chloro-2-(5-formylbenzofuran-2-yl)quinoline (0.65 g), 1-butanethiol (0.27 ml) and methyl 3-mercaptopropionate (0.24 ml) in acetonitrile (13 ml), boron trifluoride etherate (1.17 ml) was added dropwise at 0° C. After being stored in refrigerator for 18 hours, the resulting mixture was poured into ice-water, adjusted to pH 7 with aqueous sodium hydrogen carbonate solution and extracted with diethyl ether. The organic layer was washed with brine, dried over magnesium sulfate and concentrated under reduced pressure. The residue was subjected to column chromatography on silica gel and eluted with toluene, successively a mixture of toluene and ethyl acetate (8:2). The fractions containing object compound were combined and concentrated under reduced pressure to give 7-chloro-2-[5-[(buthylthio)(2-methoxycarbonylethylthio)methyl]benzofuran-2-yl]quinoline (0.42 g).

mp: 59°–60° C.

IR (Nujol): 1740, 1600, 1220 cm$^{-1}$

NMR (CDCl$_3$, δ): 0.88 (3H, t, J=7.2 Hz), 1.3–1.7 (4H, m), 2.5–3.0 (4H, m), 3.68 (3H, s), 5.07 (1H, s), 7.49 (1H, dd, J=2.2, 8.7 Hz), 7.50 (1H, dd, J=8.7, 2.2 Hz), 7.59 (1H, d, J=8.7 Hz), 7.61 (1H, s), 7.75 (1H, d, J=8.7 Hz), 7.77 (1H, d, J=2.2 Hz), 8.01 (1H, d, J=8.7 Hz), 8.20 (1H, d, J=2.2 Hz), 8.22 (1H, d, J=8.7 Hz)

MASS (m/z): 410, 380 (base), 322, 307, 292, 280

EXAMPLE 42

The following compound was obtained according to a similar manner to that of Example 41.

7-Chloro-2-[5-{[2-(dimethylcarbamoyl)ethylthio][2-(1H-tetrazol-5-yl)ethylthio]methyl}benzofuran-2-yl]-quinoline mp: 155°–158° C.

IR (Nujol): 2700, 1605, 1550 cm$^{-1}$

NMR (DMSO-d$_6$, δ): 2.6–3.1 (6H, m), 2.79 (3H, s), 2.89 (3H, s), 3.21 (2H, t, J=7.2 Hz), 5.44 (1H, s), 7.52 (1H, dd, J=2.2, 8.7 Hz), 7.67 (1H, dd, J=2.1, 8.7 Hz), 7.75 (1H, d, J=8.7 Hz), 7.85 (1H, d, J=2.1 Hz), 7.89 (1H, s), 8.08 (1H, d, J=8.7 Hz), 8.15 (1H, d, J=2.2 Hz), 8.18 (1H, d, J=8.7 Hz), 8.56 (1H, d, J=8.7 Hz)

FAB-MASS (m/z): 553 (M+1), 423, 420

EXAMPLE 43

To a cooled mixture of 7-chloro-2-(5-formylbenzofuran-2-yl)quinoline (0.77 g), N,N-dimethyl-3-mercaptopropionamide (0.37 g) and methyl 4-mercaptobutyrate (0.37 g) in acetonitrile (15 ml), boron trifluoride etherate (1.38 ml) was added dropwise at 0° C. After being stored in refrigerator for 18 hours, the resulting mixture was poured into ice-water, adjusted to pH 7 with aqueous sodium hydrogen carbonate solution and extracted with diethyl ether. The organic layer was washed with brine, dried over magnesium sulfate and concentrated under reduced pressure to give a mixture containing 3 compounds. The mixture was subjected to column chromatography on silica gel and eluted with toluene, successively a mixture of toluene and ethyl acetate (8:2) and at last a mixture of chloroform and methanol (10:1). The fractions eluted with toluene were concentrated under reduced pressure to give an oil of 7-chloro-2-{5-[bis(3-methoxycarbonylpropylthio)methyl]-benzofuran-2-yl}quinoline (0.25 g).

IR (Film): 1740, 1600 cm$^{-1}$

NMR (CDCl$_3$, δ): 1.91 (4H, sext, J=7.2 Hz), 2.41 (4H, t, J=7.2 Hz), 2.5 –2.8 (4H, m), 3.64 (6H, s), 5.02 (1H, s), 7.4–7.6 (4H, m), 7.7–7.8 (2H, m), 7.99 (1H, d, J=8.7 Hz), 8.19 (1H, d, J=2.2 Hz), 8.21 (1H, d, J=8.7 Hz)

FAB-MASS (m/z): 558 (M$^+$), 424, 324

The fractions eluted with a mixture of toluene and ethyl acetate were concentrated under reduced pressure give an oil of 7-chloro-2-[5-{[2-(dimethylcarbamoyl)-ethylthio](3-methoxycarbonylpropylthio)methyl}benzofuran-2-yl]quinoline (0.73 g).

IR (Film): 1740, 1645, 1600, 1560, 1500 cm$^{-1}$

NMR (CDCl$_3$, δ): 1.91 (2H, sext, J=7.2 Hz), 2.45 (2H, t, J=7.2 Hz), 2.51–2.76 (4H, m), 2.9–3.0 (2H, m), 2.92 (3H, s), 2.94 (3H, s), 3.65 (3H, s), 5.10 (1H, s), 7.46–7.61 (4H, m), 7.75 (1H, d, J=8.7 Hz), 8.77 (1H, d, J=2.2 Hz), 7.99 (1H, d, J=8.7 Hz), 8.19 (1H, d, J=2.2 Hz), 8.21 (1H, d, J=8.7 Hz)

MASS (m/z): 424, 322, 101

The fractions eluted with a mixture of chloroform and methanol were concentrated under reduced pressure to give an oil of 7-chloro-2-[5-(bis[2-(dimethylcarbamoyl)-ethylthio]methyl)benzofuran-2-yl]quinoline (0.4 g).

EXAMPLE 44

The following compounds were obtained according to a similar manner to that of Example 43.

1) 7-Chloro-2-{5-[bis(2-methoxycarbonylethylthio)-methyl]benzofuran-2-yl}quinoline IR (Nujol): 1740, 1600 cm$^{-1}$ NMR (CDCl$_3$, δ): 2.57 (4H, t, J=8.8 Hz), 2.7–3.0 (4H, m), 3.68 (6H, s), 5.14 (1H, s), 7.48 (2H, dd, J=2, 8 Hz), 7.59 (1H, d, J=8.6 Hz), 7.58 (1H, s), 7.75 (1H, d, J=8.5 Hz), 7.78 (1H, s), 8.00 (1H, d, J=8.5 Hz), 8.21 (1H, d, J=8.5 Hz), 8.19 (1H, s)

MASS (m/z)): 410, 322

7-Chloro-2-[5-{[2-(dimethylcarbamoyl)ethylthio](2-methoxycarbonylethylthio)methyl}benzofuran-2-yl]-quinoline IR (Film): 1740, 1640, 1600, 1490 cm$^{-1}$ NMR (CDCl$_3$, δ): 2.5–2.7 (4H, m), 2.7–3.0 (4H, m), 2.91 (1H, s), 2.93 (1H, s), 3.67 (3H, s), 5.16 (1H, s), 7.5–7.6 (2H, m), 7.59 (1H, d, J=8.6 Hz), 7.58 (1H, s), 7.75 (1H, d, J=S.6 Hz), 7.78 (1H, d, J=2.0 Hz), 8.00 (1H, d, J=8.6 Hz), 8.20 (1H, s), 8.22 (1H, d, J=8.6 Hz)

MASS (m/z): 542 (M$^+$), 410 (base), 322, 292

7-Chloro-2-[5-{bis[2-(dimethylcarbamoyl)ethylthio]-methyl}benzofuran-2-yl]quinoline IR (Film): 1640, 1600 cm$^{-1}$ NMR (CDCl$_3$, δ): 2.5–2.7 (4H, m), 2.7–3.0 (4H, m), 2.91 (12H, s), 5.18 (1H, s), 7.49 (2H, dd, J=2.0, 8.6 Hz), 7.58 (1H, d, J=8.6 Hz), 7.56 (1H, s), 7.75 (1H, d, J=8.5 Hz), 7.79 (1H, d, J=2.6 Hz), 7.99 (1H, d, J=8.6 Hz), 8–20 (1H, s), 8.22 (1H, d, J=8.6 Hz)

MASS (m/z): 555 (M$^+$), 454, ;424, 324, 298

2) 7-Chloro-2-[5-{[2-(dimethylcarbamoyl)ethylthio](4-ethoxycarbonylbutylthio)methyl}benzofuran-2-yl]-quinoline IR (Film): 1730, 1643, 1600, 1268, 845 cm$^{-1}$ NMR (CDCl$_3$, δ): 1.24 (3H, t, J=7.1 Hz), 1.52–1.80 (4H, m), 2.28 (2H, t, J=7.1 Hz), 2.50–2.70 (4H, m), 2.91 (3H, s), 2.92 (3H, s), 2.92–3.03 (2H, m), 4.11 (2H, q, J=7.1 Hz), 5.10 (1H, s), 7.48–7.54 (2H, m), 7.57–7.79 (4H, m), 8.02 d, J=8.6 Hz), 8.25 (2H, d, J=8.6 Hz)

FAB-MASS (m/z): 585 (M$^+$I), 452, 423, 324

7-Chloro-2-(5-[bis(4-ethoxycarbonylbutylthio)methyl]-benzofuran-2-yl]quinoline

IR (Film): 1738, 1723, 1600, 1266, 1180, 845 cm$^{-1}$

NMR (CDCl$_3$, δ): 1.24 (6H, t, J=7.1 Hz), 1.58–1.75 (8H, m), 2.28 (4H, t, J=7.1 Hz), 2.51–2.70 (4H, m), 4.11 (4H, q, J=7.1 Hz), 5.02 (1H, s), 7.48–7.61 (3H, m), 7.69–7.79 (3H, m), 8.03 (1H, d, J=8.7 Hz), 8.24 (2H, d, J=8.3 Hz)

MASS (m/z): 452 (base), 3.22, 292, 129

3) 7-Chloro-2-[5-{[2-(dimethylcarbamoyl)ethylthio]-(ethoxycarbonylmethylthio)methyl}benzofuran-2-yl]-quinoline mp: 122°–124° C.

IR (Nujol): 1721, 1642, 1600, 1273, 1130, 852 cm$^{-1}$

NMR (CDCl$_3$, δ): 1.28 (3H, t, J=7.1 Hz), 2.62 (2H, t, J=7.3Hz), 2.94 (6H, s), 2.94–3.42 (4H, m), 4.16 (2H, q, J=7.1 Hz), 5.33 (1H, s), 7.50 (1H, dd, J=2.0, 8.7 Hz), 7.52 (1H, dd, J=1.8, 8.6 Hz), 7.57–7.80 (4H, m), 8.01 (1H, d, J=8.7 Hz), 8.21–8.25 (2H, m)

MASS (m/z): 307

7-Chloro-2-{5-[bis(ethoxycarbonylmethylthio)methyl]-benzofuran-2-yl}quinoline mp: 106°–107° C.

IR (Nujol): 1735, 1595, 1173, 820 cm$^{-1}$

NMR (CDCl$_3$, δ): 1.28 (6H, t, J=7.1 Hz), 3.21 (2H, d, J=15.1 Hz), 3.47 (2H, d, J=15.1 Hz), 4.16 (4H, q, J=7.1 Hz), 5.50 (1H, s), 7.49 (1H, dd, J=2.0, 8.7 Hz), 7.51 (1H, dd, J=1.8, 8.7 Hz), 7.59–7.62 (2H, m), 7.74–7.81 (2H, m), 8.00 (1H, d, J=8.7 Hz), 8.20–8.25 (2H, m)

MASS (m/z): 529

4) 2-[5-{[2-(Dimethylcarbamoyl)ethylthio](2-methoxycarbonylethylthio)methyl}benzofuran-2-yl]quinoline IR (Film): 1730, 1640, 1600 cm$^{-1}$ NMR (CDCl$_3$, δ): 2.50–2.65 (4H, m), 2.74–3.01 (4H, m), 2.91 (3H, s), 2.92 (3H, s), 3.68 (3H, s), 5.16 (1H, s), 7.50 (1H, dd, J=8.7, 1.8 Hz), 7.55–7.65 (3H, m), 7.70–7.90 (3H, m), 8.02 (1H, d, J=8.6 Hz), 8.21 (1H, d, J=9.3 Hz), 8.26 (1H, d, MASS (m/z): 508 (M$^+$)

2-[5-{Bis(2-methoxycarbonylethylthio)methyl}-benzofuran-2-yl]quinoline

IR (Film): 1730, 1600 cm$^{-1}$

NMR (CDCl$_3$, δ): 2.60 (4H, t, J=7.0 Hz), 2.80–2.95 (4H, m), 3.68 (6H, s), 5.14 (1H, s), 7.48 (1H, dd, J=8.5, 1.9 Hz), 7.55–7.63 (3H, m), 7.72–7.85 (3H, m), 8.02 (1H, d, J=8.6 Hz), 8.20 (1H, d, J=9.3 Hz), 8.25 (1H, d, J=8.6 Hz)

MASS (m/z): 495 (M$^+$)

5) 7-Chloro-2-[7-{[2-(dimethylcarbamoyl)ethylthio](2-methoxycarbonylethylthio)methyl}benzofuran-2-yl]-quinoline mp: 91°–95° C.

IR (Nujol): 1735, 1720, 1650, 1620 cm$^{-1}$

NMR (CDCl$_3$, δ): 2.59 (2H, t, J=7.4 Hz), 2.68 (2H, t, J=7.3 Hz), 2.89 (6H, s), 2.80–3.09 (4H, m), 3.64 (3H, s), 5.79 (1H, s), 7.29 (1H, t, J=7.6 Hz), 7.50 (1H, dd, J=8.7, 2.0 Hz), 7.60 (1H, dd, J=7.6, 1.1 Hz), 7.62 (1H, dd, J=7.6, 1.1 Hz), 7.68 (1H, s), 7.78 (1H, d, J=8.7 Hz), 8.11 (1H, d, J=8.6 Hz), 8.15 (1H, d, J=2.0 Hz), 8.25 (1H, d, J=8.6 Hz)

MASS (m/z): 542 (M$^+$)

7-Chloro-2-[7-{bis(2-methoxycarbonylethylthio)-methyl}benzofuran-2-yl]quinoline mp: 113°–115° C.

IR (Nujol): 1745, 1730, 1620 cm$^{-1}$

NMR (CDCl$_3$, δ): 2.67 (4H, t, J=7.0 Hz), 2.80–3.07 (4H, m), 3.65 (6H, s), 5.77 (1H, s), 7.30 t, J=7.6 Hz), 7.50 (1H, dd, J=8.7, 2.0 Hz), 7.59 (1H, dd, J=7.6, 1.2 Hz), 7.63 (1H, dd, J=7.6, 1.2 Hz), 7.69 (1H, s), 7.78 (1H, d, J=8.7 Hz), 8.11 (1H, d, J=8.5 Hz), 8.16 (1H, d, J=2.0 Hz), 8.26 (1H, d, J=8.5 Hz)

MASS (m/z): 529 (M$^+$)

7-Chloro-2-[7-(bis[2-[dimethylcarbamoyl)ethylthio]-methyl]benzofuran-2-yl]quinoline mp: 93°–100° C.

IR (Nujol): 1650, 1620 cm$^{-1}$

NMR (CDCl$_{3, δ}$): 2.60 (4H, t, J=7.3 Hz), 2.89 (12H, s), 2.90–3.12 (4H, m), 5.80 (1H, s), 7.28 (1H, t, J=7.7 Hz), 7.49 (1H, dd, J=8.7, 2.0 Hz), 7.60 (2H, d, J=7.7 Hz), 7.67 (1H, s), 7.77 (1H, d, J=8.7 Hz), 8.10 (1H, d, J=8.6 Hz), 8.14 (1H, d, J=2.0 Hz), 8.24 (1H, d, J=8.6 Hz)

MASS (m/z): 555 (M$^+$)

6) 7-Chloro-2-[2-{[2-(dimethylcarbamoyl)ethylthio](3-methoxycarbonylpropylthio)methyl}benzofuran-5-yl]-quinoline IR (Film): 1730, 1640, 1610, 1600 cm$^{-1}$ NMR (CDCl$_3$, δ): 1.77–2.05 (2H, m), 2.44 (2H, t, J=7.2 Hz), 2.59 (2H, t, J=7.2 Hz), 2.60–2.87 (2H, m), 2.91–3.08 (2H, m), 2.91 (3H, s), 2.93 (3H, s), 3.65 (3H, s), 5.21 (1H, s), 6.87 (1H, s), 7.47 (1H, dd, J=8.6, 2.0 Hz), 7.60.(1H, d, J=8.6 Hz), 7.77 (1H, d, J=8.6 Hz), 7.91 (1H, d, J=B.6 Hz), 8.12 (1H, d, J=8.6, 1.8 Hz), 8.17 (1H, d, J=2.0 Hz), 8.20 (1H, d, J=8.6 Hz), 8.32 (1H, d, J=1.8 Hz)

MASS (m/z): 556 (M$^+$), 323

7-Chloro-2-[2-{bis[2-(dimethylcarbamoyl)ethylthio]-methyl}benzofuran-5-yl]quinoline IR (Film): 1640 cm$^{-1}$ NMR (CDCl$_3$, δ): 2.61 (4H, t, J=7.2 Hz), 2.92–3.14 (4H, m), 2.92 (12H, s), 5.30 (1H, s), 6.89 (1H, s), 7.47 (1H, dd, J=8.6, 2.0 Hz), 7.59 (1H, d, J=8.7 Hz), 7.76.(1H, d, J=8.6 Hz), 7.90 (1H, d, J=8.6 Hz), 8.12 (1H, dd, J=8.7, 1.7 Hz), 8.17 (1H, d, J=2.0 Hz), 8.20 (1H, d, J=8.8 Hz), 8.31 (1H, d, J=1.7 Hz)

MASS (m/z): 323

7-Chloro-2-[2-{bis(3-methoxycarbonylpropylthio)-methyl}benzofuran-5-yl]quinoline IR (Film): 1730, 1610, 1600 cm$^{-1}$ NMR (CDCl$_3$, δ): 1.86–2.05 (4H, m), 2.44 (4H, t, J=7.2 Hz), 2.60–2.87 (4H, m), 3.65 (6H, s), 5.13 (1H, s), 6.85 (1H, s), 7.47 (1H, dd, J=8.6, 2.0 Hz), 7.60 (1H, d, J=8.7 Hz), 7.76 (1H, d, J=8.6 Hz), 7.90 (1H, d, J=8.6 Hz), 8.11 (1H, dd, J=8.7, 1.8 Hz), 8.17 (1H, d, J=2.0 Hz), 8.20 (1H, d, J=8.6 Hz), 8.33 (1H, d, J=1.8 Hz)

MASS (m/Z): 266

EXAMPLE 45

To a solution of 7-chloro-2-[5-{[2-(dimethylcarbamoyl) ethylthio](3-methoxycarbonylpropylthio)methyl}-benzofuran-2-yl]quinoline (0.49 g) in methanol (5 ml), 1N aqueous lithium hydroxide (1.32 ml) was added at ambient temperature under nitrogen atmosphere. After being stirred for 15 hours at ambient temperature, the resulting mixture was concentrated under reduced pressure to give a syrup. The syrup was dissolved in water, washed with diethyl ether, adjusted to pH 4 with diluted aqueous hydrochloric acid, and extracted with ethyl acetate. The organic layer was washed with brine, dried over magnesium sulfate and concentrated under reduced pressure to give a syrup. The syrup was subjected to column chromatography on silica gel and eluted with a mixture of chloroform and methanol. The fractions containing object compound were combined and concentrated in reduced pressure to give a syrup of 7-chloro-2-[5-{(3-carboxypropylthio)[2-(dimethylcarbamoyl)ethylthio] methyl}benzofuran-2-yl]quinoline (0.35 g).

IR (Film): 2600, 1725, 1620 cm$^{-1}$

NMR (CDCl$_3$, δ: 1.8–2.2 (2H, m), 2.4–2.5 (2H, m), 2.55 (2H, t, J=7.0 Hz), 2.72 (2H, t, J=7.2 Hz), 2.8–3.2 (2H, m), 2.96 (3H, s), 2.98 (3H, s), 5.17 (1H, s), 7.45–7.60 (4H, m), 7.74 (1H, d, J=8.8 Hz), 7.78 (1H, d, J=1.3 Hz), 7.98 (1H, d, J=8.6 Hz), 8.17 (1H, d), 8.19 (1H, d, J=8.8 Hz)

FAB-MASS (m/z): 543 (M$^+$+1), 565 (M$^+$+Na), 581 (M$^+$+ K), 423, 410

EXAMPLE 46

The following compounds were obtained according to a similar manner to that of Example 45.

1) 7-Chloro-2-[5-[(butylthio)(2-carboxyethylthio)-methyl] benzofuran-2-yl]quinoline mp: 114°–116° C.

IR (Nujol): 2600, 1730, 1605 cm$^{-1}$

NMR (CDCl$_3$, δ): 0.87 (3H, s), 1.2–1.6 (4H, m), 2.4–3.0 (4H, m); 5.07 (1H, s), 7.5–7.6 (4H, m), 7.75 (1H, d, J=8.7 Hz), 7.77 (1H, d, J=2.2 Hz), 8.01 (1H, d, J=8.7 Hz), 8.18 (1H, d, J=2.2 Hz), 8.21 (1H, d, J=8.7 Hz)

FAB-MASS (m/z): 486 (M$^+$), 396, 380, 324, 307

2) 7-Chloro-2-[5-{(4-carboxybutylthio)[2-(dimethyl-carbamoyl)ethylthio]methyl}benzofuran-2-yl]quinoline IR (Film): 1725, 1600, 1266, 750 cm$^{-1}$ NMR (CDCl$_3$, δ): 1.60–1.90 (4H, m), 2.32–2.42 (2H, m), 2.57–2.65 (4H, m), 2.83–3.03 (8H, m), 5.07 (1H, s), 7.46–7.60 (4H, m), 7.73–7.78 (2H, m), 7.99 (1H, d, J=8.6 Hz), 8.21 (2H, d, J=8.9 Hz)

FAB-MASS (m/z): 557 (M +1), 555

3) 7-Chloro-2-[5-{(carboxyethylthio)[2-(dimethyl-carbamoyl)ethylthio]methyl}benzofuran-2-yl]quinoline mp: 145°–148° C.

IR (Nujol): 1728, 1600, 1115, 820 cm$^{-1}$

NMR (CDCl$_3$, δ): 2.65–2.71 (2H, m), 2.95–3.10 (2H, m), 2.97 (6H, s), 3.19 (1H, d, J=15.1 Hz), 3.45 (1H, d, J=15.1 Hz), 5.39 (1H, s), 5.99 (1H, br s), 7.46 (1H, dd, J=2.0, 8.6 Hz), 7.54–7.59 (3H, m), 7.71 (1H, d, J=8.7 Hz), 7.80 (1H, s), 7.93 (1H, d, J=8.5 Hz), 8.17 (2H, d, J=8.8 Hz)

MASS (m/z): 381, 307

4) 7-Chloro-2-{5-[bis(carboxymethylthio)methyl]-benzofuran-2-yl}quinoline mp: 208°–210° C.

IR (Nujol): 1715, 1285, 825 cm$^{-1}$

NMR (DMSO-d$_6$, δ): 3.29 (2H, d, J=15.4 Hz), 3.46 (2H, d, J=15.4 Hz), 5.45 (1H, s), 7.49 (1H, dd, J=1.8, 8.6 Hz), 7.67 (1H, dd, J=2.1, 8.7 Hz), 7.74–7.83 (2H, m), 7.90 (1H, s), 8.07–8.21 (3H, m), 8.57 (1H, d, J=8.7 Hz), 12.71 (2H, s)

MASS (m/z): 474, 381, 307 (base)

5) 7-Chloro-2-[7-{(2-carboxyethylthio)[2-(dimethyl-carbamoyl)ethylthio]methyl}benzofuran-2-yl]quinoline IR (Nujol): 2600, 1725, 1600 cm$^{-1}$ NMR (CDCl$_3$, δ): 1.7–2.2 (2H, br m), 2.45–3.2 (6H, br m), 2.83 (6H, s), 4.8–5.2 (1H, br s), 7.2–8.4 (9H, m)

FAB-MASS (m/z): 567 (M$^+$+K), 551 (M$^+$+Na), 527 (M$^+$– 1)

6) 7-Chloro-2-[5-(2-carboxyethylthiomethyl)benzofuran-2-yl]quinoline mp: 138°–155° C.

IR (Nujol): 1730, 1600 cm$^{-1}$

NMR (CDCl$_3$, δ): 2.42 (2H, t, J=6.3 Hz), 2.61 (2H, t, J=6.3 Hz), 3.90 (2H, s), 7.46 (1H, d, J=8 Hz), 7.66–7.76 (3H, m), 7.86 (1H, s), 8.09 (1H, d, J=8.5 Hz), 8.14 (1H, d, J=2.0 Hz), 8.20 (1H, d, J=8.3 Hz), 8.57 (1H, d, J=8.3 Hz)

MASS (m/z): 292

7) 7-Chloro-2-[2-{(3-carboxypropylthio)[2-(dimethylcarbamoyl)ethylthio]methyl}benzofuran-5-yl] quinoline IR (Film): 1720, 1640, 1600 cm$^{-1}$ NMR (CDCl$_3$, δ): 1.84–2.16 (2H, m), 2.40–2.51 (2H, m), 2.60–2.80 (4H, m), 2.90–3.20 (2H, m), 2.97 (3H, s), 2.98 (3H, s), 5.27 (1H, s), 6.87 (1H, s), 7.47 (1H, dd, J=8.7, 2.1 Hz), 7.60 (1H, d, J=8.7 Hz), 7.76 (1H, d, J=8.7 Hz), 7.90 (1H, d, J=8.6 Hz), 8.10 (1H, dd, J=8.7, 1.8 Hz), 8.18 (1H, d, J=2.1 Hz), 8.20 (1H, d, J=8.6 Hz), 8.32 (1H, d, J=18 Hz)

MASS (m/z) : 307

8) 7-Chloro-2-[5-{(2-carboxyethylthio)[2-(dimethyl-carbamoyl)ethylthio]methyl}benzofuran-2-yl]quinoline IR (Film): 1730, 1640, 1600, 1490 cm$^{-1}$ NMR (CDCl$_3$, δ): 2.6–3.2 (8H, m), 2.93 (6H, s), 5.20 (1H, s), 7.49 (1H, dd, J=2.0, 8.6 Hz), 7.50–7.55 (1H, m), 7.52 (1H, s), 7.55 (1H, d, J=8.6 Hz), 7.71 (1H, d, J=8.6 Hz), 7.77 (1H, d, J=1.2 Hz), 7.93 (1H, d, J=8.6 Hz), 8.1–8.2 (2H, m)

FAB-MASS (m/z): 527 (M-1), 459, 305

9) 7-Chloro-2-{5-[bis(4-carboxybutylthio)methyl]-benzofuran-2-yl}quinoline mp: 118°–124° C.

IR (Nujol): 1708, 1600, 1070 cm$^{-1}$

NMR (CDCl$_3$, δ): 1.60–1.90 (8H, m), 2.30–2.74 (8H, m), 5.03 (1H, s), 5.20–7.20 (2H, m), 7.45–7.60 (4H, m), 7.72–7.76 (2H, m), 7.98 (1H, d, J=8.6 Hz), 8.19 (2H, d, J=8.7 Hz)

EXAMPLE 47

To a suspension of 5-[2-[2-[2-(7-chloroquinolyl)]-benzofuran-5-yloxy]methyl]benzyl-1H-tetrazole (0.128 g) in methanol (30 ml), 0.1N aqueous sodium hydroxide (2.728 g) was added at ambient temperature. After being stirred under reflux for 30 minutes, the resulting solution was concentrated under reduced pressure to give a syrup. The syrup was dissolved in methanol (3.0 ml) and concentrated under reduced pressure to give crystals. The resulting crystals Were washed with ethyl acetate to give the sodium salt of 5-[2-[2-[2-(7-chloroquinolyl)]benzofuran-5-yloxy]-methyl]benzyl-1H-tetrazole (148.0 mg).

mp: 176°–181° C.

IR (Nujol): 3650, 1655, 1600 cm$^{-1}$

NMR (DMSO-d$_6$, δ): 4.12 (2H, s), 5.39 (2H, s), 7.14 (1H, dd, J=2.5, 9.0 Hz), 7.16–7.22 (3H, m), 7.37 (1H, m), 7.43–7.45 (1H, m), 7.66 (1H, d, J=9.0 Hz), 7.66 (1H, dd, J=2.1, 8.8 Hz)., 7.79 (1H, s), 8.08 (1H, d, J=8.8 Hz), 8.16 (1H, d, J=2.1 Hz), 8.17 (1H, d, J=8.7 Hz), 8.55 (1H, d, J=8.7 Hz)

FAB-MASS (m/z): 490 ((M+H)$^+$)

We claim:

1. A compound of the formula:

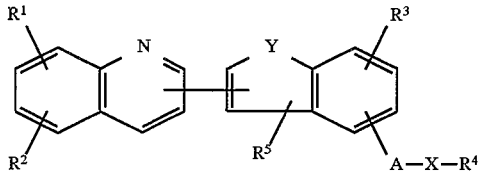

(I)

where $R^1$ is halogen, $R^2$ is hydrogen, $R^3$ is hydrogen, $R^4$ is hydrogen, lower alkanoyl, lower alkoxycarbonyl (lower) alkanoyl or lower alkyl which may be substituted with substituent (s) selected from the group consisting of hydroxy, carboxy, lower alkoxycarbonyl, tetrazolylcarbamoyl, lower (alkyl) carbamoyl, arylsulfonylcarbamoyl, carboxy (lower) alkylthio, lower alkylthio, tetrazolyl (lower) alkyl, lower alkoxycarbonyl (lower) alkylthio, lower alkylcarbamoyl (lower) alkylthio and aryl optionally substituted with halo (lower) alkyl, cyano (lower) alkyl, tetrazolyl (lower) alkyl, cyano, carboxy, lower alkoxycarbonyl, arylsulfonylcarbamoyl, tetrazolylcarbamoyl or tetrazolyl, $R^5$ is hydrogen, A is a single bond X is a single bond, O or NH, and Y is O.

2. A compound according to claim 1, wherein $R^4$ is lower alkyl which is substituted with aryl substituted with tetrazolyl(lower)alkyl or tetrazolyl, and X is O.

3. The compound 5-[2-[2-[2-(7-chloroquinolyl)] benzofuran-5-yloxy]-methyl]benzyl-1H-tetrazole or its salt.

4. A pharmaceutical composition comprising a compound of claim 1, as an active ingredient, in association with a pharmaceutically acceptable, non-toxic carrier or excipient.

5. A method for the therapeutic treatment and/or prevention of allergy or inflammation which comprises administering an effective amount of a compound of claim 1 to human beings or animals.

* * * * *